(12) United States Patent
Tucker

(10) Patent No.: US 7,192,973 B2
(45) Date of Patent: Mar. 20, 2007

(54) PIPERIDINE DERIVATIVES AND THEIR USE AS MODULATORS OF CHEMOKINE RECEPTOR ACTIVITY (ESPECIALLY CCR5)

(75) Inventor: Howard Tucker, Macclesfield (GB)

(73) Assignee: AstraZeneca AB (SE)

( * ) Notice: Subject to any disclaimer, the term of this patent is extended or adjusted under 35 U.S.C. 154(b) by 148 days.

(21) Appl. No.: 10/495,196

(22) PCT Filed: Nov. 12, 2002

(86) PCT No.: PCT/SE02/02055

§ 371 (c)(1),
(2), (4) Date: May 11, 2004

(87) PCT Pub. No.: WO03/042205

PCT Pub. Date: May 22, 2003

(65) Prior Publication Data

US 2004/0267016 A1    Dec. 30, 2004

(30) Foreign Application Priority Data

Nov. 15, 2001 (SE) .................................... 0103818

(51) Int. Cl.
*A61K 31/445* (2006.01)
*C07D 401/04* (2006.01)
(52) U.S. Cl. ..................... 514/316; 546/187
(58) Field of Classification Search ............... 546/184, 546/187; 514/316
See application file for complete search history.

(56) References Cited

U.S. PATENT DOCUMENTS

| | | | |
|---|---|---|---|
| 3,203,992 A | 8/1965 | Kunz et al. | |
| 3,577,432 A | 5/1971 | Helsley et al. | |
| 3,755,584 A | 8/1973 | Plotnikoff et al. | |
| 3,818,017 A | 6/1974 | Janssen et al. | |
| 3,894,030 A | 7/1975 | Janssen et al. | |
| 4,029,801 A | 6/1977 | Cavalla et al. | |
| 4,105,666 A | 8/1978 | Ward | |
| 4,105,771 A | 8/1978 | Archibald et al. | |
| 4,166,119 A | 8/1979 | Effland et al. | |
| 4,246,267 A | 1/1981 | Vincent et al. | |
| 4,264,613 A | 4/1981 | Regnier et al. | |
| 4,338,323 A | 7/1982 | Regnier et al. | |
| 5,576,321 A | 11/1996 | Krushinski, Jr. et al. | |
| 5,614,523 A | 3/1997 | Audia et al. | |
| 5,614,533 A | 3/1997 | Anderson et al. | |
| 5,627,196 A | 5/1997 | Audia et al. | |
| 5,688,960 A | 11/1997 | Shankar | |
| 5,696,267 A | 12/1997 | Reichard et al. | |
| 5,741,789 A | 4/1998 | Hibschman et al. | |
| 5,789,402 A | 8/1998 | Audia et al. | |
| 5,840,725 A | 11/1998 | Reichard et al. | |
| 6,790,854 B2 | 9/2004 | Tsushima et al. | |
| 6,958,350 B2 | 10/2005 | Brough et al. | |
| 6,960,602 B2 | 11/2005 | Burrows et al. | |
| 2002/0094989 A1 | 7/2002 | Hale et al. | |

FOREIGN PATENT DOCUMENTS

| | | |
|---|---|---|
| DE | 37 23 568 A1 | 1/1989 |
| DE | 197 03 131 A1 | 7/1998 |
| DE | 197 55 268 A1 | 6/1999 |
| EP | 0 077 427 | 4/1983 |
| EP | 0 095 454 | 11/1983 |
| EP | 0 128 007 | 12/1984 |
| EP | 0 228 893 | 7/1987 |
| EP | 0 235 463 | 9/1987 |
| EP | 0 290 958 | 11/1988 |
| EP | 0 354 568 A2 | 2/1990 |
| EP | 0 407 217 A1 | 1/1991 |
| EP | 0 445 862 B1 | 9/1991 |
| EP | 0 457 686 B1 | 11/1991 |
| EP | 0 496 691 A1 | 7/1992 |
| EP | 0 587 311 A1 | 3/1994 |
| EP | 0 625 507 B1 | 11/1994 |
| EP | 0 643 057 A1 | 3/1995 |
| EP | 0 722 941 A2 | 7/1996 |
| EP | 0 903 349 A2 | 3/1999 |
| EP | 1013276 A1 | 6/2000 |

(Continued)

OTHER PUBLICATIONS

Cohen et al., Am. J. Clin. Pathol., 1996, 105 (5), 589.*

*Primary Examiner*—Celia Chang
(74) *Attorney, Agent, or Firm*—Fish & Richardson P.C.

(57) ABSTRACT

Compounds of formula (I): wherein L is CH or N; M is CH or N; provided that L and M are not both CH; compositions comprising them, processes for preparing them and their use in medical therapy (for example modulating CCR5 receptor activity in a warm blooded animal)

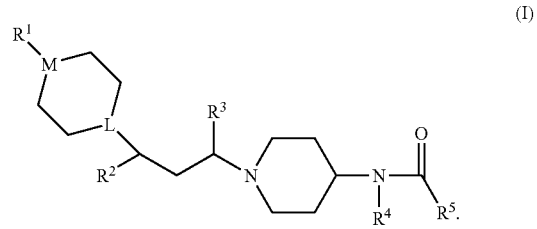

11 Claims, No Drawings

FOREIGN PATENT DOCUMENTS

| | | |
|---|---|---|
| EP | 1 277 737 | 1/2003 |
| FR | 2 096 916 | 3/1972 |
| FR | 2 190 430 | 2/1974 |
| GB | 1368012 | 9/1974 |
| GB | 1 404 868 | 9/1975 |
| GB | 1425354 | 2/1976 |
| GB | 1 532 671 | 11/1978 |
| GB | 1 538 542 | 1/1979 |
| GB | 1 544 191 | 4/1979 |
| JP | 63-264525 | 11/1988 |
| JP | 10259176 | 9/1998 |
| WO | WO 92/02502 | 2/1992 |
| WO | WO 92/15579 | 9/1992 |
| WO | WO 93/13083 | 7/1993 |
| WO | WO 93/15052 | 8/1993 |
| WO | WO 93/25528 | 12/1993 |
| WO | WO 94/27967 | 12/1994 |
| WO | WO 95/11880 | 5/1995 |
| WO | WO 96/19452 | 6/1996 |
| WO | WO 96/26205 | 8/1996 |
| WO | WO 96/34857 | 11/1996 |
| WO | WO 96/39386 | 12/1996 |
| WO | WO 97/10207 | 3/1997 |
| WO | WO 97/10212 | 3/1997 |
| WO | WO 97/19060 | 5/1997 |
| WO | WO 97/23458 | 7/1997 |
| WO | WO 97/47299 | 12/1997 |
| WO | WO 98/02151 | 1/1998 |
| WO | WO 98/08826 | 3/1998 |
| WO | WO 98/31364 | 7/1998 |
| WO | WO 98/31366 | 7/1998 |
| WO | WO 98/32442 | 7/1998 |
| WO | WO 98/51311 | 11/1998 |
| WO | WO 99/04794 | 2/1999 |
| WO | WO 99/17773 | 4/1999 |
| WO | WO 99/25686 | 5/1999 |
| WO | WO 99/27928 | 6/1999 |
| WO | WO 99/27929 | 6/1999 |
| WO | WO 99/28314 | 6/1999 |
| WO | WO 99/31092 | 6/1999 |
| WO | WO 99/37304 | 7/1999 |
| WO | WO 99/37619 A1 | 7/1999 |
| WO | WO 99/38514 | 8/1999 |
| WO | WO 97/42956 | 11/1999 |
| WO | WO 99/64394 | 12/1999 |
| WO | WO 99/65895 | 12/1999 |
| WO | WO 00/08013 | 2/2000 |
| WO | WO 00/21948 | 4/2000 |
| WO | WO 00/21952 | 4/2000 |
| WO | WO 00/23076 | 4/2000 |
| WO | WO 00/35449 | 6/2000 |
| WO | WO 00/35451 | 6/2000 |
| WO | WO 00/39108 | 7/2000 |
| WO | WO 00/53600 | 9/2000 |
| WO | WO 00/58305 | 10/2000 |
| WO | WO 00/61559 | 10/2000 |
| WO | WO 00/69820 | 11/2000 |
| WO | WO 00/76511 | 12/2000 |
| WO | WO 00/76512 | 12/2000 |
| WO | WO 00/76513 | 12/2000 |
| WO | WO 00/76514 | 12/2000 |
| WO | WO 00/76972 | 12/2000 |
| WO | WO 00/76973 A1 | 12/2000 |
| WO | WO 01/14333 A1 | 3/2001 |
| WO | WO 01/19817 | 3/2001 |
| WO | WO 01/43744 | 6/2001 |
| WO | WO 01/44227 | 6/2001 |
| WO | WO 01/66525 | 9/2001 |
| WO | WO 01/87839 A1 | 11/2001 |
| WO | WO 01/90106 | 11/2001 |
| WO | WO 01/92227 A1 | 12/2001 |
| WO | WO 02/066460 | 8/2002 |
| WO | WO 02/070479 | 9/2002 |
| WO | WO 02/076948 | 10/2002 |
| WO | WO 02/079156 | 10/2002 |
| WO | WO 03/030898 | 4/2003 |
| WO | WO 2004/099178 | 4/2003 |
| WO | WO 03/042177 | 5/2003 |
| WO | WO 03/042178 | 5/2003 |
| WO | WO 2004/056773 | 7/2004 |
| WO | WO 03/080574 | 8/2005 |
| WO | WO 2004/056808 | 3/2006 |
| WO | WO 2004/056809 | 3/2006 |

* cited by examiner

PIPERIDINE DERIVATIVES AND THEIR USE AS MODULATORS OF CHEMOKINE RECEPTOR ACTIVITY (ESPECIALLY CCR5)

CROSS-REFERENCE TO RELATED APPLICATIONS

This application is the national phase application under 35 U.S.C. §371 of PCT International Application No. PCT/SE02/02055, filed Nov. 12, 2002, which claims priority to SE 0103818-1, filed Nov. 15, 2001. These applications are incorporated by reference herein in their entirety.

The present invention relates to heterocyclic derivatives having pharmaceutical activity, to processes for preparing such derivatives, to pharmaceutical compositions comprising such derivatives and to the use of such derivatives as active therapeutic agents.

Pharmaceutically active piperidine derivatives are disclosed in PCT/SE01/01053, EP-A1-1013276, WO00/08013, WO99/38514 and WO99/04794.

Chemokines are chemotactic cytokines that are released by a wide variety of cells to attract macrophages, T cells, eosinophils, basophils and neutrophils to sites of inflammation and also play a role in the maturation of cells of the immune system. Chemokines play an important role in immune and inflammatory responses in various diseases and disorders, including asthma and allergic diseases, as well as autoimmune pathologies such as rheumatoid arthritis and atherosclerosis. These small secreted molecules are a growing superfamily of 8–14 kDa proteins characterised by a conserved four cysteine motif. The chemokine superfamily can be divided into two main groups exhibiting characteristic structural motifs, the Cys-X-Cys (C—X—C, or α) and Cys-Cys (C—C, or β) families. These are distinguished on the basis of a single amino acid insertion between the NH-proximal pair of cysteine residues and sequence similarity.

The C—X—C chemokines include several potent chemoattractants and activators of neutrophils such as interleukin-8 (IL8) and neutrophil-activating peptide 2 (NAP-2).

The C—C chemokines include potent chemoattractants of monocytes and lymphocytes but not neutrophils such as human monocyte chemotactic proteins 1–3 (MCP-1, MCP-2 and MCP-3), RANTES (Regulated on Activation, Normal T Expressed and Secreted), eotaxin and the macrophage inflammatory proteins 1α and 1β (MIP-1α and MIP-1β).

Studies have demonstrated that the actions of the chemokines are mediated by subfamilies of G protein-coupled receptors, among which are the receptors designated CCR1, CCR2, CCR2A, CCR2B, CCR3, CCR4, CCR5, CCR6, CCR7, CCR8, CCR9, CCR10, CXCR1, CXCR2, CXCR3 and CXCR4. These receptors represent good targets for drug development since agents which modulate these receptors would be useful in the treatment of disorders and diseases such as those mentioned above.

The CCR5 receptor is expressed on T-lymphocytes, monocytes, macrophages, dendritic cells, microglia and other cell types. These detect and respond to several chemokines, principally "regulated on activation normal T-ell expressed and secreted" (RANTES), macrophage inflammatory proteins (MIP) MIP-1α and MP-1β and monocyte chemoattractant protein-2 (MCP-2).

This results in the recruitment of cells of the immune system to sites of disease. In many diseases it is the cells expressing CCR5 which contribute, directly or indirectly, to tissue damage. Consequently, inhibiting the recruitment of these cells is beneficial in a wide range of diseases.

CCR5 is also a co-receptor for HIV-1 and other viruses, allowing these viruses to enter cells. Blocking the receptor with a CCR5 antagonist or inducing receptor internalisation with a CCR5 agonist protects cells from viral infection.

The present invention provides a compound of formula (I):

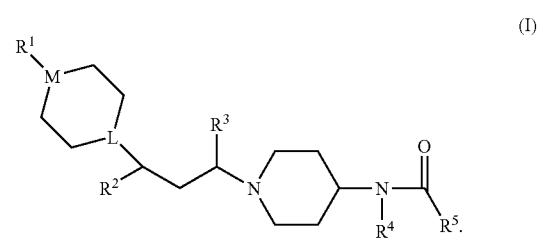

wherein

L is CH or N; M is CH or N; provided that L and M are not both CH;

$R^1$ is hydrogen, $C_{1-6}$ alkyl [optionally substituted by phenyl {which itself optionally substituted by halo, $C_{1-4}$ alkyl, $C_{1-4}$ alkoxy, cyano, nitro, $CF_3$, $OCF_3$, ($C_{1-4}$ alkyl)C(O)NH, $S(O)_2NH_2$, $C_{1-4}$ alylthio, $S(O)(C_{1-4}$ alkyl) or $S(O)_2(C_{1-4}$ alkyl)} or heteroaryl {which itself optionally substituted by halo, $C_{1-4}$ alkyl, $C_{1-4}$ alkoxy, cyano, nitro, $CF_3$, ($C_{1-4}$ alkyl)C(O)NH, $S(O)_2NH_2$, $C_{1-4}$ alkylthio, $S(O)(C_{1-4}$ alkyl) or $S(O)_2(C_{1-4}$ alkyl)}], phenyl {optionally substituted by halo, $C_{1-4}$ alkyl, $C_{1-4}$ alkoxy, cyano, nitro, $CF_3$, $OCF_3$, ($C_{1-4}$ alkyl)C(O)NH, $S(O)_2NH_2$, $C_{1-4}$ alkylthio, $S(O)(C_{1-4}$ alkyl) or $S(O)_2(C_{1-4}$ alkyl)}, heteroaryl {optionally substituted by halo, $C_{1-4}$ alkyl, $C_{1-4}$ alkoxy, cyano, nitro, $CF_3$, ($C_{1-4}$ alkyl)C(O)NH, $S(O)_2NH_2$, $C_{1-4}$ alkylthio, $S(O)(C_{1-4}$ alkyl) or $S(O)_2(C_{1-4}$ alkyl)}, $S(O)_2R^6$, $S(O)_2NR^{10}R^{11}$, $C(O)R^7$, $C(O)_2(C_{1-6}$ alkyl) (such as tert-butoxycarbonyl), $C(O)_2(phenyl(C_{1-2}$ alkyl)) (such as benzyloxycarbonyl) or $C(O)NHR^7$; and when M is CH $R^1$ can also be $NHS(O)_2R^6$, $NHS(O)_2NHR^7$, $NHC(O)R^7$ or $NHC(O)NHR^7$;

$R^2$ is phenyl or heteroaryl, either of which is optionally substituted by halo, $C_{1-4}$ alkyl, $C_{1-4}$ alkoxy, $S(O)_n(C_{1-4}$ alkyl), nitro, cyano or $CF_3$;

$R^3$ is hydrogen or $C_{1-4}$ alkyl;

$R^4$ is hydrogen, methyl, ethyl, allyl or cyclopropyl;

$R^5$ is phenyl, heteroaryl, phenylNH, heteroarylNH, phenyl($C_{1-2}$)alkyl, heteroaryl($C_{1-2}$)alkyl, phenyl($C_{1-2}$ alkyl)NH or heteroaryl($C_{1-2}$ alkyl)NH; wherein the phenyl and heteroaryl rings of $R^5$ are optionally substituted by halo, cyano, nitro, hydroxy, $C_{1-4}$ alkyl, $C_{1-4}$ alkoxy, $S(O)_k(C_{1-4}$ alkyl), $S(O)_2NR^8R^9$, $NHS(O)_2(C_{1-4}$ alkyl), $NH_2$, $NH(C_{1-4}$ alkyl), $N(C_{1-4}$ alkyl)$_2$, $NHC(O)NH_2$, $C(O)NH_2$, $C(O)NH(C_{1-4}$ alkyl), $NHC(O)(C_{1-4}$ alkyl), $CO_2H$, $CO_2(C_{1-4}$ alkyl), $C(O)(C_{1-4}$ alkyl), $CF_3$, $CHF_2$, $CH_2F$, $CH_2CF_3$ or $OCF_3$;

k, m and n are, independently, 0, 1 or 2;

$R^6$ is $C_{1-6}$alkyl [optionally substituted by halo (such as fluoro), $C_{1-4}$ alkoxy, phenyl {which itself optionally substituted by halo, $C_{1-4}$ alkyl, $C_{1-4}$ alkoxy, cyano, nitro, $CF_3$, $OCF_3$, ($C_{1-4}$ alkyl)C(O)NH, $S(O)_2NH_2$, $C_{1-4}$ alkylthio, $S(O)(C_{1-4}$ alkyl) or $S(O)_2(C_{1-4}$ alkyl)} or heteroaryl {which itself optionally substituted by halo, $C_{1-4}$ alkyl, $C_{1-4}$ alkoxy, cyano, nitro, $CF_3$, ($C_{1-4}$ alkyl)C(O)NH, $S(O)_2NH_2$, $C_{1-4}$ alkylthio, $S(O)(C_{1-4}$ alkyl) or $S(O)_2(C_{1-4}$ alkyl)}], $C_{3-7}$ cycloalkyl, pyranyl, phenyl {optionally substituted by halo, $C_{1-4}$ alkyl, $C_{1-4}$ alkoxy, cyano, nitro, $CF_3$, $OCF_3(C_{1-4}$ alkyl)C(O)NH, $S(O)_2NH_2$, $C_{1-4}$ alylthio, $S(O)(C_{1-4}$ alkyl) or $S(O)_2(C_{1-4}$ alkyl)} or heteroaryl {optionally substituted by halo, $C_{1-4}$ alkyl, $C_{1-4}$ alkoxy, cyano, nitro, $CF_3$, $(C_{1-4}$ alkyl)C(O)NH, $S(O)_2NH_2$, $C_{1-4}$ alkylthio, $S(O)(C_{1-4}$ alkyl) or $S(O)_2(C_{1-4}$ alkyl)};

$R^7$ is hydrogen, $C_{1-6}$ alkyl [optionally substituted by halo (such as fluoro), $C_{1-4}$ alkoxy, phenyl {which itself optionally substituted by halo, $C_{1-4}$ alkyl, $C_{1-4}$ alkoxy, cyano, nitro, $CF_3$, $OCF_3$, $(C_{1-4}$ alkyl)C(O)NH, $S(O)_2NH_2$, $C_{1-4}$ alkylthio, $S(O)(C_{1-4}$ alkyl) or $S(O)_2(C_{1-4}$ alkyl)} or heteroaryl {which itself optionally substituted by halo, $C_{1-4}$ alkyl, $C_{1-4}$ alkoxy, cyano, nitro, $CF_3$, $(C_{1-4}$ alkyl)C(O)NH, $S(O)_2NH_2$, $C_{1-4}$ alkylthio, $S(O)(C_{1-4}$ alkyl) or $S(O)_2(C_{1-4}$ alkyl)}], $C_{3-7}$ cycloalkyl, pyranyl, phenyl {optionally substituted by halo, $C_{1-4}$ alkyl, $C_{1-4}$ alkoxy, cyano, nitro, $CF_3OCF_3(C_{1-4}$ alkyl)C(O)NH, $S(O)_2NH_2$, $C_{1-4}$ alkylthio, $S(O)(C_{1-4}$ alkyl) or $S(O)_2(C_{1-4}$ alkyl)} or heteroaryl {optionally substituted by halo, $C_{1-4}$ alkyl, $C_{1-4}$ alkoxy, cyano, nitro, $CF_3$, $(C_{1-4}$ alkyl)C(O)NH, $S(O)_2NH_2$, $C_{1-4}$ alkylthio, $S(O)(C_{1-4}$ alkyl) or $S(O)_2(C_{1-4}$ alkyl)};

$R^8$ and $R^9$ are, independently, hydrogen or $C_{1-4}$ alkyl, or together with a nitrogen or oxygen atom, may join to form a 5- or 6-membered ring which is optionally substituted with $C_{1-4}$ alkyl, C(O)H or $C(O)(C_{1-4}$ alkyl);

$R^{10}$ and $R^{11}$ are, independently, hydrogen or $C_{1-4}$ alkyl, or may join to form a 5- or 6-membered ring which is optionally substituted with $C_{1-4}$ alkyl or phenyl (wherein the phenyl ring is optionally substituted by halo, cyano, nitro, hydroxy, $C_{1-4}$ alkyl, $C_{1-4}$ alkoxy, $S(O)_mC_{1-4}$ alkyl, $S(O)_2NH_2$, $S(O)_2NH(C_{1-4}$ alkyl), $S(O)_2N(C_{1-4}$ alkyl)$_2$, $NHS(O)_2(C_{1-4}$ alkyl), $NH_2$, $NH(C_{1-4}$ alkyl), $N(C_{1-4}$ alkyl)$_2$, $NHC(O)NH_2$, $C(O)NH_2$, $C(O)NH(C_{1-4}$ alkyl), $NHC(O)(C_{1-4}$ alkyl), $CO_2H$, $CO_2(C_{1-4}$ alkyl), $C(O)(C_{1-4}$ alkyl), $CF_3$, $CHF_2$, $CH_2F$, $CH_2CF_3$ or $OCF_3$);

or a pharmaceutically acceptable salt thereof or a solvate thereof;

provided that when $R^1$ is hydrogen or unsubstituted alkyl, $R^4$ is hydrogen, methyl or ethyl, L is CH and M is N, then the phenyl or heteroaryl part of $R^5$ is substituted by one of: $S(O)_kC_{1-4}$ alkyl, $NHC(O)NH_2$, $C(O)(C_{1-4}$ alkyl), $CHF_2$, $CH_2F$, $CH_2CF_3$ or $OCF_3$, and optionally further substituted by one or more of halo, cyano, nitro, hydroxy, $C_{1-4}$ alkyl, $C_{1-4}$ alkoxy, $S(O)_kC_{1-4}$ alkyl, $S(O)_2NR^8R^9$, $NHS(O)_2(C_{1-4}$ alkyl), $NH_2$, $NH(C_{1-4}$ alkyl), $N(C_{1-4}$ alkyl)$_2$, $NHC(O)NH_2$, $C(O)NH_2$, $C(O)NH(C_{1-4}$ alkyl), $NHC(O)(C_{1-4}$ alkyl), $CO_2H$, $CO_2(C_{1-4}$ alkyl), $C(O)(C_{1-4}$ alkyl), $CF_3$, $CHF_2$, $CH_2F$, $CH_2CF_3$ or $OCF_3$.

Certain compounds of the present invention can exist in different isomeric forms (such as enantiomers, diastereomers, geometric isomers or tautomers). The present invention covers all such isomers and mixtures thereof in all proportions.

Suitable salts include acid addition salts such as a hydrochloride, hydrobromide, phosphate, acetate, fumarate, maleate, tartrate, citrate, oxalate, methanesulphonate or p-toluenesulphonate.

The compounds of the invention may exist as solvates (such as hydrates) and the present invention covers all such solvates.

Alkyl groups and moieties are straight or branched chain and are, for example, methyl, ethyl, n-propyl, iso-propyl, n-butyl, sec-butyl or tert-butyl. Methyl is sometimes abbreviated to Me hereinbelow.

Fluoroalkyl includes, for example, one to six, such as one to three, fluorine atoms, and comprises, for example, a $CF_3$ group. Fluoroalkyl is, for example, $CF_3$ or $CH_2CF_3$.

Cycloalkyl is, for example, cyclopropyl, cyclopentyl or cyclohexyl.

Phenyl($C_{1-2}$ alkyl)alkyl is, for example, benzyl, 1-(phenyl)eth-1-yl or 1-(phenyl)eth-2-yl.

Heteroaryl($C_{1-2}$ alkyl)alkyl is, for example, pyridinylmethyl, pyrimidinylmethyl or 1-(pyridinyl)eth-2-yl.

Phenyl($C_{1-2}$ alkyl)NH is, for example, benzylamino. Heteroaryl($C_{1-2}$ alkyl)NH is, for example, pyridinyl$CH_2$NH, pyrimidinyl$CH_2$NH or pyridinyl$CH(CH_3)$NH Heteroaryl is an aromatic 5 or 6 membered ring, optionally fused to one or more other rings, comprising at least one heteroatom selected from the group comprising nitrogen, oxygen and sulphur; or an N-oxide thereof, or an S-oxide or S-dioxide thereof. Heteroaryl is, for example, furyl, thienyl (also known as thiophenyl), pyrrolyl, thiazolyl, isothiazolyl, pyrazolyl, oxazolyl, isoxazolyl, imidazolyl, [1,2,4]-triazolyl, pyridinyl, pyrimidinyl, indolyl, benzo[b]furyl (also known as benzfuryl), benz[b]thienyl (also known as benzthienyl or benzthiophenyl), indazolyl, benzimidazolyl, benztriazolyl, benzoxazolyl, benzthiazolyl, 1,2,3-benzothiadiazolyl, an imidazopyridinyl (such as imidazo[1,2a]pyridinyl), thieno [3,2-b]pyridin-6-yl, 1,2,3-bernzoxadiazolyl (also known as benzo[1,2,3]thiadiazolyl), 2,1,3-benzothiadiazolyl, benzofurazan (also known as 2,1,3-benzoxadiazolyl), quinoxalinyl, a pyrazolopyridine (for example 1H-pyrazolo[3,4b] pyridinyl), quinolinyl, isoquinolinyl, a naphthyridinyl (for example [1,6]naphthyridinyl or [1,8]naphthyridinyl), a benzothiazinyl or dibenzothiophenyl (also known as dibenzothienyl); or an N-oxide thereof, or an S-oxide or S-dioxide thereof. Heteroaryl can also be pyrazinyl. Heteroaryl is, for example, pyridinyl, pyrinidinyl, indolyl or benzimidazolyl.

In one particular aspect the present invention provides a compound of formula (I) wherein L is CH or N; M is CH or N; provided that L and M are not both CH; $R^1$ is hydrogen, $C_{1-6}$ alkyl [optionally substituted by phenyl {which itself optionally substituted by halo, $C_{1-4}$ alkyl, $C_{1-4}$ alkoxy, cyano, nitro, $CF_3$, $C_{1-4}$ alkylthio, $S(O)(C_{1-4}$ alkyl) or $S(O)_2(C_{1-4}$ alkyl)} or heteroaryl {which itself optionally substituted by halo, $C_{1-4}$ alkyl, $C_{1-4}$ alkoxy, cyano, nitro, $CF_3$, $C_{1-4}$ alkylthio, $S(O)(C_{1-4}$ alkyl) or $S(O)_2(C_{1-4}$ alkyl)}], phenyl {optionally substituted by halo, $C_{1-4}$ alkyl, $C_{1-4}$ alkoxy, cyano, nitro, $CF_3C_{1-4}$alkylthio, $S(O)(C_{1-4}$ alkyl) or $S(O)_2(C_{1-4}$ alkyl)}, heteroaryl {optionally substituted by halo, $C_{1-4}$ alkyl, $C_{1-4}$ alkoxy, cyano, nitro, $CF_3$, $C_{1-4}$ alkylthio, $S(O)(C_{1-4}$ alkyl) or $S(O)_2(C_{1-4}$ alkyl)}, $S(O)_2R^6$, $S(O)_2NHR^7$, $C(O)R^7$, $C(O)_2(C_{1-6}$ alkyl) or $C(O)NHR^7$; and when M is CH $R^1$ can also be $NHS(O)_2R^6$, $NHS(O)_2NHR^7$, $NHC(O)R^7$ or $NHC(O)NHR^7$; $R^2$ is phenyl or heteroaryl, either of which is optionally substituted in the ortho or meta position by halo, $C_{1-4}$ alkyl, $C_{1-4}$ alkoxy, $S(O)_n(C_{1-4}$ alkyl), nitro, cyano or $CF_3$; $R^3$ is hydrogen or $C_{1-4}$ alkyl; $R^4$ is hydrogen; methyl, ethyl, allyl or cyclopropyl; $R^5$ is phenyl, heteroaryl, phenylNH, heteroarylNH, phenyl($C_{1-2}$)alkyl, heteroaryl($C_{1-2}$) alkyl, phenyl($C_{1-2}$ alkyl)NH or heteroaryl($C_{1-2}$ alkyl)NH; wherein the phenyl and heteroaryl rings of $R^5$ are optionally substituted by halo, cyano, nitro, hydroxy, $C_{1-4}$ alkyl, $C_{1-4}$ alkoxy, $S(O)_kC_{1-4}$ alkyl, $S(O)_2NR^8R^9$, $NHS(O)_2(C_{1-4}$ alkyl), $NH_2$, $NH(C_{1-4}$ alkyl), $N(C_{1-4}$ alkyl)$_2$, $NHC(O)NH_2$, $C(O)NH_2$, $C(O)NH(C_{1-4}$ alkyl), $NHC(O)(C_{1-4}$ alkyl), $CO_2H$, $CO_2(C_{1-4}$ alkyl), $C(O)(C_{1-4}$ alkyl), $CF_3$, $CHF_2$, $CH_2F$, $CH_2CF_3$ or $OCF_3$; $R^8$ and $R^9$ are, independently, hydrogen or $C_{1-4}$ alkyl, or together with a nitrogen or oxygen atom, may join to form a 5- or 6-membered ring which is optionally substituted with $C_{1-4}$ alkyl, C(O)H or $C(O)(C_{1-4}$ alkyl); k and n are, independently, 0, 1 or 2; $R^6$ is $C_{1-5}$ alkyl [optionally substituted by phenyl {which itself optionally substituted by halo, $C_{1-4}$ alkyl, $C_{1-4}$ alkoxy, cyano, nitro, $CF_3$, $C_{1-4}$ alkylthio, $S(O)(C_{1-4}$ alkyl) or $S(O)_2(C_{1-4}$ alkyl)} or heteroaryl {which itself optionally substituted by halo, $C_{1-4}$ alkyl, $C_{1-4}$ alkoxy, cyano, nitro, $CF_3$, $C_{1-4}$ alkylthio, $S(O)(C_{1-4}$ alkyl) or $S(O)_2(C_{1-4}$ alkyl)}], $C_{3-7}$ cycloalkyl, phenyl {optionally substituted by halo, $C_{1-4}$ alkyl, $C_{1-4}$ alkoxy, cyano, nitro, $CF_3$, $C_{1-4}$ alkylthio, $S(O)(C_{1-4}$ alkyl) or $S(O)_2(C_{1-4}$ alkyl)} or heteroaryl {optionally substituted by halo, $C_{1-4}$ alkyl, $C_{1-4}$ alkoxy, cyano, nitro, $CF_3$, $C_{1-4}$ alkylthio, $S(O)(C_{1-4}$ alkyl) or $S(O)_2(C_{1-4}$ alkyl)}; $R^7$ is hydrogen, $C_{1-6}$ alkyl [optionally substituted by phenyl {which itself optionally substituted by halo, $C_{1-4}$ alkyl, $C_{1-4}$ alkoxy, cyano, nitro, $CF_3$, $C_{1-4}$ alkylthio, $S(O)(C_{1-4}$ alkyl) or $S(O)_2(C_{1-4}$ alkyl)} or heteroaryl {which itself optionally substituted by halo, $C_{1-4}$ alkyl, $C_{1-4}$ alkoxy, cyano, nitro, $CF_3$, $C_{1-4}$ alkylthio, $S(O)(C_{1-4}$ alkyl) or $S(O)_2(C_{1-4}$ alkyl)}], $C_{3-7}$ cycloalkyl, phenyl {optionally substituted by halo, $C_{1-4}$ alkyl, $C_{1-4}$ alkoxy, cyano, nitro, $CF_3$, $C_{1-4}$ alkylthio, $S(O)(C_{1-4}$ alkyl) or $S(O)_2(C_{1-4}$ alkyl)} or heteroaryl {optionally substituted by halo, $C_{1-4}$ alkyl, $C_{1-4}$ alkoxy, cyano, nitro, $CF_3$, $C_{1-4}$ alkylthio, $S(O)(C_{1-4}$ alkyl) or $S(O)_2(C_{1-4}$ alkyl)}; or a pharmaceutically acceptable salt thereof or a solvate thereof; provided that when $R^1$ is hydrogen or unsubstituted alkyl, $R^4$ is hydrogen, methyl or ethyl, L is CH and M is N, then the phenyl or heteroaryl part of $R^5$ is substituted by one of: $S(O)_kC_{1-4}$ alkyl, $NHC(O)NH_2$, $C(O)(C_{1-4}$ alkyl), $CHF_2$, $CH_2F$, $CH_2CF_3$ or $OCF_3$, and optionally further substituted by one or more of halo, cyano, nitro, hydroxy, $C_{1-4}$ alkyl, $C_{1-4}$ alkoxy, $S(O)_kC_{1-4}$ alkyl, $S(O)_2NR^8R^9$, $NHS(O)_2(C_{1-4}$ alkyl), $NH2$, $NH(C_{1-4}$ alkyl), $N(C_{1-4}$ alkyl)$_2$, $NHC(O)NH_2$, $C(O)NH_2$, $C(O)NH(C_{1-4}$ alkyl), $NHC(O)(C_{1-4}$ alkyl), $CO_2H$, $CO_2(C_{1-4}$ alkyl), $C(O)(C_{1-4}$ alkyl), $CF_3$, $CHF_2$, $CH_2F$, $CH_2CF_3$ or $OCF_3$.

In another aspect the present invention provides a compound of the invention wherein when L and M are both N, and $R^1$ is hydrogen, $C_{1-4}$ alkyl or phenyl (the phenyl being substituted with 0, 1 or 2 substituents selected from the list consisting of: fluoro, chloro, $C_{1-4}$ alkyl, $C_{1-4}$ alkoxy, cyano, $CF_3$, $OCF_3$, $(C_{1-4}$ alkyl)$C(O)NH$ and $S(O)_2NH_2$); then the phenyl or heteroaryl moiety of $R^5$ carries a $S(O)_2(C_{1-4}$ alkyl) substituent, and, optionally, one or more further substituents.

In a further aspect of the invention heteroaryl is pyrrolyl, thienyl, imidazolyl, thiazolyl, isoxazolyl, pyridinyl, pyrimidinyl, pyrazinyl or quinolinyl.

In another aspect M is N and L is CH or N.

In yet another aspect L and M are both N.

In a further aspect L is CH and M is N.

In a still further aspect L is N and M is CH.

In another aspect of the invention $R^1$ is hydrogen, $C_{1-6}$ alkyl [optionally substituted by phenyl {which itself optionally substituted by halo}], $S(O)_2R^6$, $S(O)_2NHR^7$, $C(O)R^7$, $C(O)_2(C_{1-6}$ alkyl) or $C(O)NHR^7$; and when M is CH $R^1$ can also be $NHS(O)_2R^6$, $NHS(O)_2NHR^7$, $NHC(O)R^7$ or $NHC(O)NHR^7$; $R^6$ is $C_{1-6}$ alkyl [optionally substituted by phenyl {which itself optionally substituted by halo}], $C_{3-7}$ cycloalkyl, phenyl {optionally substituted by halo}; and $R^7$ is hydrogen, $C_{1-6}$ alkyl [optionally substituted by phenyl {which itself optionally substituted by halo}], $C_{3-7}$ cycloalkyl, phenyl {optionally substituted by halo}.

In another aspect of the invention $R^1$ is $C_{1-6}$ alkyl [substituted by phenyl {which itself optionally substituted by halo}], $S(O)_2R^6$, $S(O)_2NHR^7$, $C(O)R^7$, $C(O)_2(C_{1-6}$ alkyl) or $C(O)NHR^7$; and when M is CH $R^1$ can also be $NHS(O)_2R^6$, $NHS(O)_2NHR^7$, $NHC(O)R^7$ or $NHC(O)NHR^7$; $R^6$ is $C_{1-6}$ alkyl [optionally substituted by phenyl {which itself optionally substituted by halo}], $C_{3-7}$ cycloallyl, phenyl {optionally substituted by halo}; and $R^7$ is hydrogen, $C_{1-6}$ alkyl [optionally substituted by phenyl {which itself optionally substituted by halo}], $C_{3-7}$ cycloalkyl, phenyl {optionally substituted by halo}.

In a further aspect of the invention $R^1$ is $S(O)_2R^6$, $C(O)R^7$, $C(O)_2(C_{1-6}$ alkyl) or $C(O)NHR^7$; and when M is CH $R^1$ can also be $NHS(O)_2R^6$ or $NHC(O)R^7$; and $R^6$ and $R^7$ are as defined above.

In another aspect of the invention $R^1$ is hydrogen, $C_{1-6}$ alkyl [optionally substituted by phenyl {which itself optionally substituted by halo}], $S(O)_2R^6$, $C(O)R^7$, $C(O)_2(C_{1-6}$ alkyl) or $C(O)NHR^7$; and when M is CH $R^1$ can also be $NHS(O)_2R^6$ or $NHC(O)R^7$; $R^6$ is $C_{1-6}$ alkyl [optionally substituted by phenyl {which itself optionally substituted by halo}], $C_{3-7}$ cycloalkyl, phenyl {optionally substituted by halo}; and $R^7$ is hydrogen, $C_{1-6}$ alkyl [optionally substituted by phenyl {which itself optionally substituted by halo}], $C_{3-7}$ cycloalkyl, phenyl {optionally substituted by halo}.

In a further aspect $R^1$ is phenyl (optionally substituted by halo (for example fluoro), $C_{1-4}$ alkyl (for example methyl), $C_{1-4}$ alkoxy (for example methoxy), $CF_3$ or $OCF_3$), $S(O)_2(C_{1-4}$ alkyl) (for example $S(O)_2CH_3$, $S(O)_2CH_2CH_3$ or $S(O)_2CH(CH_3)_2$), $S(O)_2(C_{1-4}$ fluoroalkyl) (for example $S(O)_2CF_3$ or $S(O)_2CH_2CF_3$), $S(O)_2$phenyl (optionally substituted (such as mono-substituted) by halo (for example chloro), cyano, $C_{1-4}$ alkyl, $C_{1-4}$ alkoxy, $CF_3$, $OCF_3$, $S(O)_2(C_{1-4}$ alkyl) (for example $S(O)_2CH_3$ or $S(O)_2CH_2CH_3$) or $S(O)_2(C_{1-4}$ fluoroalkyl) (for example $S(O)_2CH_2CF_3$)), benzyl (optionally substituted by halo (for example chloro or fluoro), $C_{1-4}$ alkyl, $C_{1-4}$ alkoxy (for example methoxy), $CF_3$ or $OCF_3$), benzoyl (optionally substituted by halo (for example chloro or fluoro), $C_{1-4}$ alkyl (for example methyl), $C_{1-4}$ alkoxy, $CF_3$ or $OCF_3$), $C(O)NH$phenyl (optionally substituted by halo (for example fluoro), $C_{1-4}$ alkyl, $C_{1-4}$ alkoxy, $CF_3$ or $OCF_3$), $S(O)_2$thiophenyl, $CH_2$pyridinyl, $CH_2$quinolinyl or $CH_2$thiazolyl.

In yet another aspect $R^1$ is phenyl (optionally substituted (such as mono-substituted) by halo (for example fluoro), $C_{1-4}$ alkyl (for example methyl) or $C_{1-4}$ alkoxy (for example methoxy)), $S(O)_2(C_{1-4}$ alkyl) (for example $S(O)_2CH_3$, $S(O)_2CH_2CH_3$ or $S(O)_2CH(CH_3)_2$), $S(O)_2(C_{1-4}$ fluoroalkyl) (for example $S(O)_2CF_3$ or $S(O)_2CH_2CF_3$), $S(O)_2$phenyl (optionally substituted (such as mono-substituted) by halo (for example chloro), cyano, $CF_3$, $OCF_3$, $S(O)_2(C_{1-4}$ alkyl) (for example $S(O)_2CH_3$ or $S(O)_2CH_2CH_3$) or $S(O)_2(C_{1-4}$ fluoroalkyl) (for example $S(O)_2CH_2CF_3$)), benzyl (optionally substituted by halo (for example chloro or fluoro) or $C_{1-4}$ alkoxy (for example methoxy)), benzoyl (optionally substituted by halo (for example chloro or fluoro) or $C_{1-4}$ alkyl (for example methyl)), $C(O)NH$phenyl (optionally substituted by halo (for example fluoro)), $S(O)_2$thiophenyl, $CH_2$pyridinyl, $CH_2$quinolinyl or $CH_2$thiazolyl.

In a further aspect $R^1$ is phenyl (optionally substituted (such as mono-substituted) by halo (for example fluoro) or $C_{1-4}$ alkyl (for example methyl)), $S(O)_2(C_{1-4}$ alkyl) (for example $S(O)_2CH_3$, $S(O)_2CH_2CH_3$ or $S(O)_2CH(CH_3)_2$), $S(O)_2(C_{1-4}$ fluoroalkyl) (for example $S(O)_2CF_3$ or $S(O)_2CH_2CF_3$), $S(O)_2$phenyl (optionally substituted (such as mono-substituted) by $CF_3$, $OCF_3$ or $S(O)_2(C_{1-4}$ alkyl) (for example $S(O)_2CH_3$)), benzyl (optionally substituted by halo (for example chloro or fluoro) or $C_{1-4}$ alkoxy (for example methoxy)), benzoyl (optionally substituted by halo (for example chloro or fluoro)), $C(O)NH$phenyl (optionally substituted by halo (for example fluoro)), $CH_2$pyridinyl, $CH_2$quinolinyl or $CH_2$thiazolyl.

In a still further aspect $R^1$ is hydrogen, $C_{1-6}$ alkyl [optionally substituted by phenyl {which itself optionally substituted by halo, $C_{1-4}$ alkyl, $C_{1-4}$ alkoxy, cyano, nitro, $CF_3$, $OCF_3$, $(C_{1-4}$ alkyl)$C(O)NH$, $S(O)_2NH_2$ or $S(O)_2(C_{1-4}$ alkyl)} or heteroaryl {which itself optionally substituted by halo, $C_{1-4}$ alkyl or $(C_{1-4}$ alkyl)$C(O)NH$}], phenyl {optionally substituted by halo, $C_{1-4}$ alkyl, $C_{1-4}$ alkoxy, cyano, nitro, $CF_3$, $OCF_3$, $(C_{1-4}$ alkyl)$C(O)NH$, $S(O)_2NH_2$ or $S(O)_2(C_{1-4}$ alkyl)}, heteroaryl {optionally substituted by halo, $C_{1-4}$ alkyl or $(C_{1-4}$ alkyl)$C(O)NH$}, $S(O)_2R^6$, $S(O)_2NR^{10}R^{11}$, $C(O)R^7$ or $C(O)NHR^7$; and when M is CH $R^1$ can also be $NHC(O)R^7$; $R^6$ is $C_{1-6}$ alkyl [optionally substituted by halo (such as fluoro), phenyl {which itself optionally substituted by halo, $C_{1-4}$ alkyl, $C_{1-4}$ alkoxy, cyano, nitro, $CF_3$, $OCF_3$, $(C_{1-4}$ alkyl)$C(O)NH$, $S(O)_2NH_2$ or $S(O)_2(C_{1-4}$ alkyl)) or heteroaryl {which itself optionally substituted by halo, $C_{1-4}$ alkyl or $(C_{1-4}$ alkyl)$C(O)NH$}], phenyl {optionally substituted by halo, $C_{1-4}$ alkyl, $C_{1-4}$ alkoxy, cyano, nitro, $CF_3$, $OCF_3$, $(C_{1-4}$ alkyl)$C(O)NH$, $S(O)_2NH_2$ or $S(O)_2(C_{1-4}$ alkyl)} or heteroaryl {optionally substituted by halo, $C_{1-4}$ alkyl or $(C_{1-4}$ alkyl)$C(O)NH$}; $R^7$ is hydrogen, $C_{1-6}$ alkyl [optionally substituted by halo (such as fluoro), $C_{1-4}$ alkoxy, phenyl {which itself optionally substituted by halo, $C_{1-4}$ alkyl, $C_{1-4}$ alkoxy, cyano, nitro, $CF_3OCF_3$, $(C_{1-4}$ alkyl)$C(O)NH$, $S(O)_2NH_2$ or $S(O)_2(C_{1-4}$ alkyl)} or heteroaryl {which itself optionally substituted by halo, $C_{1-4}$ alkyl or $(C_{1-4}$ alkyl)$C(O)NH$}], $C_{3-7}$ cycloalkyl, pyranyl, phenyl {optionally substituted by halo, $C_{1-4}$ alkyl, $C_{1-4}$ alkoxy, cyano, nitro, $CF_3$, $OCF_3$, $(C_{1-4}$ alkyl)$C(O)NH$, $S(O)NH_2$ or $S(O)_2(C_{1-4}$ alkyl)} or heteroaryl {optionally substituted by halo, $C_{1-4}$ alkyl or $(C_{1-4}$ alkyl)$C(O)NH$}; and, $R^{10}$ and $R^{11}$ are, independently, hydrogen or $C_{1-4}$ alkyl.

In a further aspect $R^1$ is phenyl (optionally substituted (such as mono-substituted) by halo (for example fluoro) or $C_{1-4}$ alkyl (for example methyl)), $S(O)_2(C_{1-4}$ alkyl) (for example $S(O)_2CH_3$ or $S(O)_2CH_2CH_3$), $S(O)_2(C_{1-4}$ fluoroalkyl) (for example $S(O)_2CF_3$), $S(O)_2$phenyl (optionally substituted (such as mono-substituted) by $CF_3$ or $OCF_3$), benzyl, benzoyl (optionally substituted by halo (for example chloro or fluoro)) or $C(O)NH$phenyl (optionally substituted by halo (for example fluoro)).

In yet another aspect of the invention $R^2$ is phenyl or heteroaryl, either of which is optionally substituted in the ortho or meta position by halo, $C_{1-4}$ alkyl, $C_{1-4}$ alkoxy, $S(O)_n(C_{1-4}$ alkyl), nitro, cyano or $CF_3$; wherein n is 0, 1 or 2, for example 0 or 2. (Ortho and meta positions are ortho and meta relative to the position of attachment of that ring to the structure of formula (I).)

In a still further aspect $R^2$ is optionally substituted phenyl (such as optionally substituted by halo (such as chloro or fluoro), cyano, methyl, ethyl, methoxy, ethoxy or $CF_3$). In one aspect the substitution is on the ortho or meta position of the phenyl ring.

In another aspect $R^2$ is optionally substituted phenyl (such as optionally substituted by halo or $CF_3$). For example $R^2$ is 3-fluorophenyl, 3-chlorophenyl, 4-fluorophenyl or 4-$CF_3$-phenyl. In a further aspect $R^2$ is phenyl, 3-fluorophenyl, 4fluorophenyl, 3-chlorophenyl, 3,4-difluorophenyl or 3,5-difluorophenyl. In another aspect $R^2$ is phenyl, 3-fluorophenyl, 4-fluorophenyl, 3,4-difluorophenyl or 3,5-difluorophenyl. In a still further aspect of the invention $R^2$ is phenyl or 3-fluorophenyl.

In another aspect of the invention $R^3$ is hydrogen or methyl. In a further aspect of the invention when $R^3$ is $C_{1-4}$ alkyl (such as methyl) the carbon to which $R^3$ is attached has the R absolute configuration. In yet another aspect of the invention $R^3$ is hydrogen.

In a further aspect of the invention $R^4$ is ethyl.

In a still further aspect the present invention provides a compound of the invention wherein $R^5$ is phenyl($C_{1-2}$)alkyl, phenyl($C_{1-2}$ alkyl)NH, phenyl, heteroaryl or heteroaryl ($C_{1-2}$)alkyl; wherein the phenyl and heteroaryl rings are optionally substituted by halo, cyano, nitro, hydroxy, $C_{1-4}$ alkyl, $C_{1-4}$ alkoxy, $S(O)_kC_{1-4}$ alkyl, $S(O)_2NR^8R^9$, $NHS(O)_2(C_{1-4}$ alkyl), $NH_2$, $NH(C_{1-4}$ alkyl), $N(C_{1-4}$ alkyl)$_2$, $NHC(O)NH_2$, $C(O)NH_2$, $C(O)NH(C_{1-4}$ alkyl), $NHC(O)(C_{1-4}$ alkyl), $CO_2H$, $CO_2(C_{1-4}$ alkyl), $C(O)(C_{1-4}$ alkyl), $CF_3$, $CHF_2$, $CH_2F$, $CH_2CF_3$ or $OCF_3$; and $R^8$ and $R^9$ are, independently, hydrogen or $C_{1-4}$ alkyl, or together with a nitrogen or oxygen atom, may join to form a 5- or 6-membered ring which is optionally substituted with $C_{1-4}$ alkyl, $C(O)H$ or $C(O)(C_{1-4}$ alkyl); and k is 0, 1 or 2 (for example, 2).

In another aspect the invention provides a compound of the invention wherein $R^5$ is phenyl($C_{1-2}$)alkyl or phenyl($C_{1-2}$ alkyl)NH; wherein the phenyl rings of $R^5$ are optionally substituted by halo, cyano, nitro, hydroxy, $C_{1-4}$ alkyl, $C_{1-4}$ alkoxy, $S(O)_kC_{1-4}$ alkyl, $S(O)_2NR^8R^9$, $NHS(O)_2(C_{1-4}$ alkyl), $NH_2$, $NH(C_{1-4}$ alkyl), $N(C_{1-4}$ alkyl)$_2$, $NHC(O)NH_2$, $C(O)NH_2$, $C(O)NH(C_{1-4}$ alkyl), $NHC(O)(C_{1-4}$ alkyl), $CO_2H$, $CO_2(C_{1-4}$ alkyl), $C(O)(C_{1-4}$ alkyl), $CF_3$, $CHF_2$, $CH_2F$, $CH_2CF_3$ or $OCF_3$; $R^8$ and $R^9$ are, independently, hydrogen or $C_{1-4}$ alkyl together with a nitrogen or oxygen atom, may join to form a 5- or 6-membered ring which is optionally substituted with $C_{1-4}$ alkyl, $C(O)H$ or $C(O)(C_{1-4}$ alkyl); and k is 0, 1 or 2.

In a still further aspect of the invention $R^5$ is phenyl, heteroaryl, phenyl($C_{1-2}$)alkyl or heteroaryl($C_{1-2}$)alkyl; wherein the phenyl and heteroaryl rings are optionally substituted by halo, cyano, nitro, hydroxy, $C_{1-4}$ alkyl, $C_{1-4}$ alkoxy, $S(O)_kC_{1-4}$ alkyl, $S(O)_2NR^8R^9$, $NHS(O)_2(C_{1-4}$ alkyl), $NH_2$, $NH(C_{1-4}$ alkyl), $N(C_{1-4}$ alkyl)$_2$, $NHC(O)NH_2$, $C(O)NH_2$, $C(O)NH(C_{1-4}$ alkyl), $NHC(O)(C_{1-4}$ alkyl), $CO_2H$, $CO_2(C_{1-4}$ alkyl), $C(O)(C_{1-4}$ alkyl), $CF_3$, $CHF_2$, $CH_2F$, $CH_2CF_3$ or $OCF_3$; k is 0, 1 or 2; and $R^8$ and $R^9$ are, independently, hydrogen or $C_{1-4}$ alkyl, or together with a nitrogen or oxygen atom, may join to form a 5- or 6-membered ring which is optionally substituted with $C_{1-4}$ alkyl, $C(O)H$ or $C(O)(C_{1-4}$ alkyl).

In another aspect $R^5$ is phenyl or benzyl; wherein the aromatic rings are optionally substituted by halo, cyano, nitro, hydroxy, $C_{1-4}$ alkyl, $C_{1-4}$ alkoxy, $S(O)_kC_{1-4}$ alkyl, $S(O)_2NR^8R^9$, $NHS(O)_2(C_{1-4}$ alkyl), $NH^2$, $NH(C_{1-4}$ alkyl), $N(C_{1-4}$ alkyl)$_2$, $NHC(O)NH_2$, $C(O)NH_2$, $C(O)NH(C_{1-4}$ alkyl), $NHC(O)(C_{1-4}$ alkyl), $CO_2H$, $CO_2(C_{1-4}$ alkyl), $C(O)(C_{1-4}$ alkyl), $CF_3$, $CHF_2$, $CH_2F$, $CH_2CF_3$ or $OCF_3$; k is 0, 1 or 2; and $R^8$ and $R^9$ are, independently, hydrogen or $C_{1-4}$ alkyl, or together with a nitrogen or oxygen atom, may join to form a 5- or 6-membered ring which is optionally substituted with $C_{1-4}$ alkyl, $C(O)H$ or $C(O)(C_{1-4}$ alkyl).

In a further aspect $R^5$ is phenyl or benzyl; wherein the aromatic rings are optionally substituted by halo, cyano, nitro, hydroxy, $C_{1-4}$ alkyl, $C_{1-4}$ alkoxy, $S(O)_2C_{1-4}$ alkyl, $S(O)_2NR^8R^9$, $NHS(O)_2(C_{1-4}$ alkyl), $NH_2$, $NH(C_{1-4}$ alkyl), $N(C_{1-4}$ alkyl)$_2$, $NHC(O)NH_2$, $C(O)NH_2$, $C(O)NH(C_{1-4}$ alkyl), $NHC(O)(C_{1-4}$ alkyl), $CO_2H$, $CO_2(C_{1-4}$ alkyl), $C(O)(C_{1-4}$ alkyl), $CF_3$; and $R^8$ and $R^9$ are, independently, hydrogen or $C_{1-4}$ alkyl.

In another aspect $R^5$ is $NHCH_2$phenyl wherein the phenyl ring is optionally substituted by halo, cyano, nitro, hydroxy, $C_{1-4}$ alkyl, $C_{1-4}$ alkoxy, $S(O)_2C_{1-4}$ alkyl, $S(O)_2NR^8R^9$, $NHS(O)_2(C_{1-4}$ alkyl), $NH_2$, $NH(C_{1-4}$ alkyl), $N(C_{1-4}$ alkyl)$_2$, $NHC(O)NH_2$, $C(O)NH_2$, $C(O)NH(C_{1-4}$ alkyl), $NHC(O)(C_{1-4}$ alkyl), $CO_2H$, $CO_2(C_{1-4}$ alkyl), $C(O)(C_{1-4}$ alkyl), $CF_3$; and $R^8$ and $R^9$ are, independently, hydrogen or $C_{1-4}$ alkyl.

In yet another aspect R⁵ is benzyl wherein the phenyl ring is optionally substituted by halo, cyano, nitro, hydroxy, C₁₋₄ alkyl, C₁₋₄ alkoxy, S(O)₂C₁₋₄ alkyl, S(O)₂NR⁸R⁹, NHS(O)₂ (C₁₋₄ alkyl), NH₂, NH(C₁₋₄ alkyl), N(C₁₋₄ alkyl)₂, NHC(O) NH₂, C(O)NH₂, C(O)NH(C₁₋₄ alkyl), NHC(O)(C₁₋₄ alkyl), CO₂H, CO₂(C₁₋₄ alkyl), C(O)(C₁₋₄ alkyl), CF₃; and R⁸ and R⁹ are, independently, hydrogen or C₁₋₄ alkyl.

In another aspect R⁵ is NHCH₂phenyl wherein the aromatic ring is optionally substituted by halo (such as fluoro, chloro or bromo), cyano, C₁₋₄ alkyl (such as methyl), C₁₋₄ alkoxy (such as methoxy) or S(O)₂C₁₋₄ alkyl (such as S(O)₂CH₃).

In yet another aspect R⁵ is benzyl wherein the aromatic ring is optionally substituted by halo (such as fluoro, chloro or bromo), cyano, C₁₋₄ alkyl (such as methyl), C₁₋₄ alkoxy (such as methoxy) or S(O)₂C₁₋₄ alkyl (such as S(O)₂CH₃).

In a still further aspect R⁵ is phenyl or benzyl, wherein the aromatic ring is substituted (for example in the para-position) by S(O)₂C₁₋₄ alkyl and the ring is optionally further substituted by halo, cyano, nitro, hydroxy, C₁₋₄ alkyl or C₁₋₄ alkoxy.

In another aspect R⁵ is NHCH₂phenyl or benzyl, wherein the aromatic ring is substituted (for example in the para-position) by S(O)₂C₁₋₄ alkyl (such as S(O)₂CH₃) and the ring is optionally further substituted by halo, cyano, nitro, hydroxy, C₁₋₄ alkyl or C₁₋₄ alkoxy.

In another aspect R⁵ is NHCH₂phenyl wherein the aromatic ring is substituted (for example in the para-position) by S(O)₂C₁₋₄ alkyl (such as S(O)₂CH₃), R⁵ is, for example NHCH₂(4-S(O)₂CH₃—C₆H₄).

In another aspect R⁵ is benzyl, wherein the aromatic ring is substituted (for example in the para-position) by S(O)₂ C₁₋₄ alkyl (such as S(O)₂CH₃), R⁵ is, for example CH₂(4-S (O)₂CH₃—C₆H₄).

The carbon labelled ^ in the representation of formula (I) shown below, is always chiral.

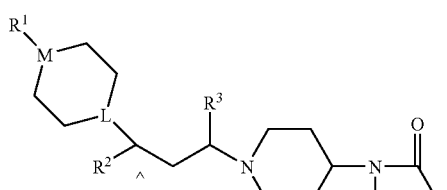
(I)

When L is N the carbon labelled ^ has, for example, the S absolute configuration. When L is CH the carbon labelled ^ has, for example, the R absolute configuration.

In another aspect the present invention provides a compound of formula (Ia):

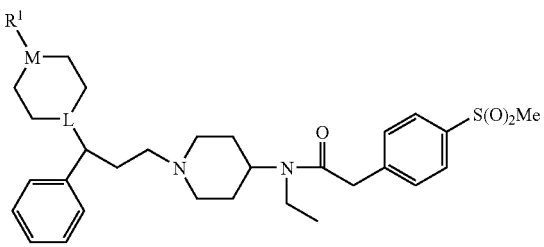
(Ia)

wherein L, M and R¹ are as defined above.

In a further aspect the present invention provides a compound of formula (Ib):

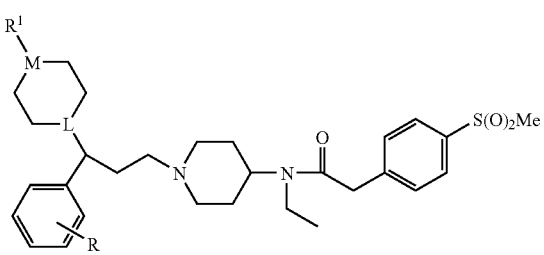
(Ib)

wherein L, M and R¹ are as defined above; and R is hydrogen, one or two fluorine atoms, S(O)ₙ(C₁₋₄ alkyl) or C₁₋₄ alkoxy; and n is 0, 1 or 2 (for example, 2).

In another aspect the present invention provides a compound of formula (Ic):

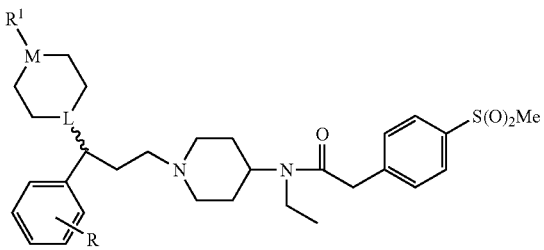
(Ic)

wherein L, M and R¹ are as defined above; and R is hydrogen, one or two fluorine atoms, S(O)ₙ(C₁₋₄ alkyl) or C₁₋₄ alkoxy; and n is 0, 1 or 2 (for example, 2).

In a still further aspect the present invention provides a compound of formula (Id):

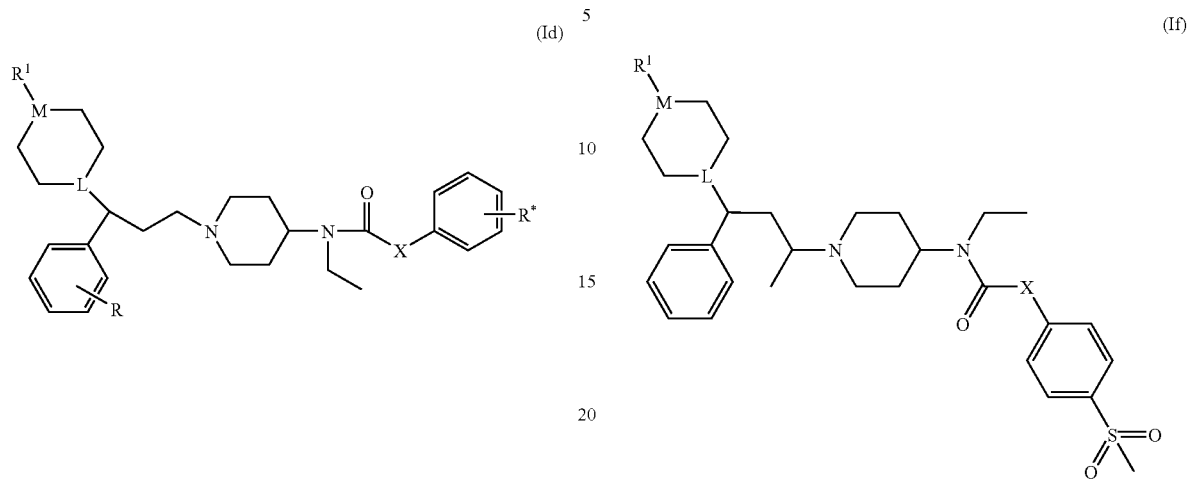

wherein L, M and $R^1$ are as defined above; R is hydrogen, one or two fluorine atoms, $S(O)_n(C_{1-4}$ alkyl) or $C_{1-4}$ alkoxy; X is $NHCH_2$, NH or $CH_2$; n is 0, 1 or 2 (for example, 2); and R* is halo (such as fluoro, chloro or bromo), cyano, $C_{1-4}$ alkyl (such as methyl), $C_{1-4}$ alkoxy (such as methoxy) or $S(O)_2C_{1-4}$ alkyl (such as $S(O)_2CH_3$).

In another aspect the present invention provides a compound of formula (Ie):

wherein L, M, X and $R^1$ are as defined above.

In a still further aspect the present invention provides a compound of formula (Ig):

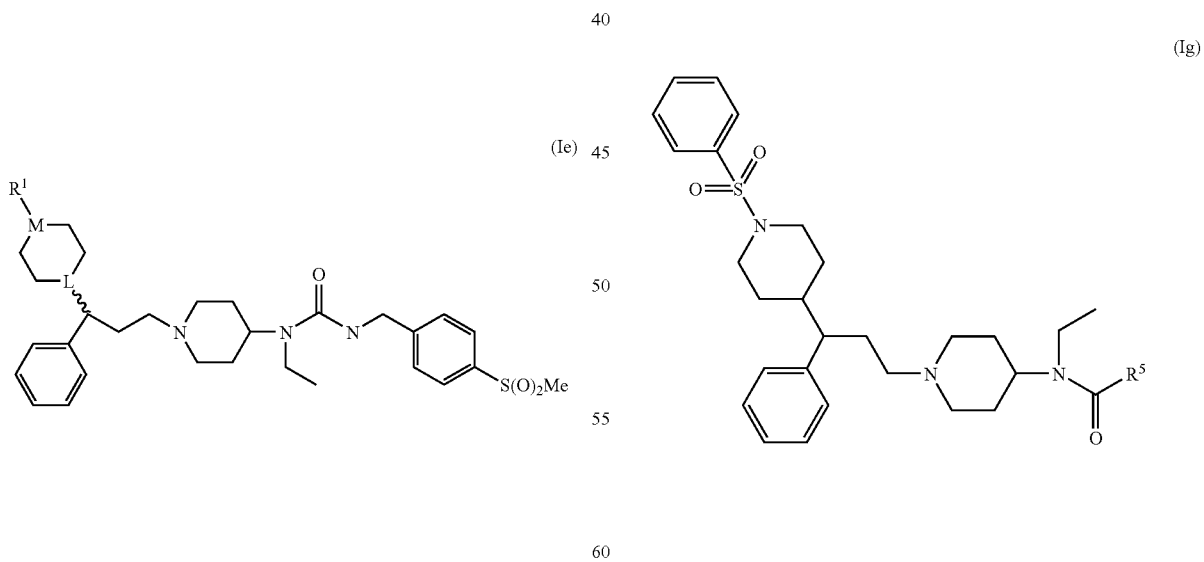

wherein L, M and $R^1$ are as defined above.

In yet another aspect the present invention provides a compound of formula (If):

wherein $R^5$ is as defined above.

The compounds listed in Tables I to VI illustrate the invention

TABLE I

Table I comprises compounds of formula (Ib).

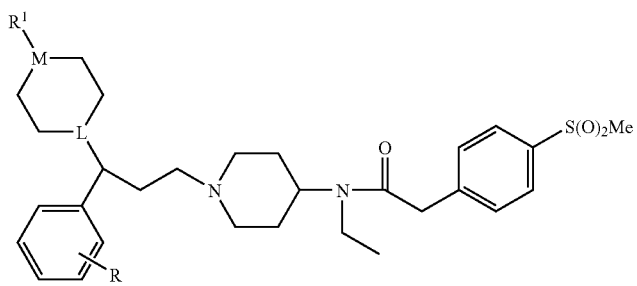

(Ib)

| Compound No. | L | M | R | R¹ | LCMS (MH+) |
|---|---|---|---|---|---|
| 1 | N | N | H | Formyl | 555 |
| 2 | N | N | H | iso-butyryl | 597 |
| 3 | N | N | H | Acetyl | 569 |
| 4 | N | N | H | Benzoyl | 631 |
| 5 | N | N | H | Ethyl | 555 |
| 6 | N | N | H | Methyl | 541 |
| 7 | N | N | H | Benzenesulfonyl | 667 |
| 8 | N | CH | H | Benzyl | 616 |
| 9 | N | CH | H | Acetyl | 568 |
| 10 | N | CH | H | Benzylaminocarbonyl | 659 |
| 11 | N | CH | H | Ethoxycarbonyl | 598 |
| 12 | N | CH | H | Methyl | 540 |
| 13 | N | CH | H | Phenylacetylamino | 659 |
| 14 | N | CH | H | Acetylamino | 583 |
| 15 | N | CH | H | Methanesulfonylamino | 618 |
| 16 | N | CH | H | Benzenesulfonylamino | 681 |
| 17 | CH | N | H | H | 526 |
| 18 | CH | N | H | Benzyl | 616 |
| 19 | CH | N | H | Phenylacetyl | 644 |
| 20 | CH | N | H | iso-butyryl | 596 |
| 21 | CH | N | H | Acetyl | 568 |
| 22 | CH | N | H | Cyclohexylaminocarbonyl | 651 |
| 23 | CH | N | H | tert-butyloxycarbonyl | 626 |
| 24 | CH | N | H | 4-Chlorobenzoyl | 664 |
| 25 | CH | N | H | Ethyl | 554 |
| 26 | CH | N | H | Methyl | 540 |
| 27 | CH | N | H | Ethanesulfonyl | 618 |
| 28 | CH | N | H | Methanesulfonyl | 604 |
| 29 | N | CH | H | Phenylureido | 660 |
| 30 | N | CH | H | iso-propylaminocarbonyl | 611 |
| 31 | N | CH | H | 4-Chlorophenylaminocarbonyl | 679 |
| 32 | N | CH | H | 4-Fluorophenylaminocarbonyl | 663 |
| 33 | N | CH | H | 4-Chlorobenzoylamino | 679 |
| 34 | N | N | H | Phenylaminocarbonyl | 546 |
| 35 | N | N | H | Propylaminocarbonyl | 612 |
| 36 | N | N | H | Methanesulfonyl | 605 |
| 37 | N | N | H | Ethanesulfonyl | 619 |
| 38 | N | N | H | 1-Methylethanesulfonyl | 633 |
| 39 | N | N | H | Phenylmethanesulfonyl | |
| 40 | N | N | H | Benzenesulfonyl (S-isomer) | |
| 41 | CH | N | H | Benzoyl | |
| 42 | CH | N | H | Benzenesulfonyl | |
| 43 | CH | N | H | iso-propylsulfonyl | |
| 44 | CH | N | H | Phenylaminocarbonyl | |
| 45 | N | N | H | phenyl | 603 |
| 46 | N | N | H | 4-fluorophenyl | 621 |
| 47 | N | N | H | 4-methoxyphenyl | 633 |
| 48 | N | N | H | 2-chlorophenyl | 637 |
| 49 | N | N | H | 4-chlorophenyl | 637 |
| 50 | N | N | H | 3-chlorophenyl | 637 |
| 51 | N | N | H | 2-fluorophenyl | 637 |
| 52 | N | N | H | 4-methanesulphonylbenzoyl | 709 |
| 53 | N | N | H | 2-methanesulphonylbenzensulphonyl | 745 |
| 54 | N | N | H | 3-methanesulphonylbenzoyl | 709 |
| 55 | N | N | H | 3-fluorophenyl | 621 |
| 56 | N | N | 3-fluoro | phenyl | 621 |
| 57 | N | N | 3-fluoro | 4-methanesuphonylphenyl | 699 |

TABLE I-continued

Table I comprises compounds of formula (Ib).

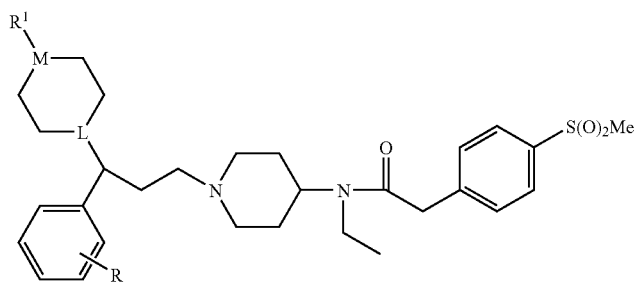
(Ib)

| Compound No. | L | M | R | R¹ | LCMS (MH+) |
|---|---|---|---|---|---|
| 58 | N | N | 3-fluoro | benzenesulphonyl | 685 |
| 59 | N | N | 3-fluoro | 4-methanesulphonylbenzenesulphonyl | 763 |
| 60 | N | N | 3-fluoro | ethanesulphonyl | 637 |
| 61 | N | N | 3-fluoro | methanesulphonyl | 623 |
| 62 | N | N | 3-fluoro | 4-chlorophenyl | 655 |
| 63 | N | N | 3-fluoro | 3-chlorophenyl | 655 |
| 64 | N | N | 3-fluoro | 2-fluorophenyl | 639 |
| 65 | N | N | 3-fluoro | 4-fluorophenyl | 639 |
| 66 | N | N | H | 5-Bromopyrimidin-2-yl | 683 |
| 67 | N | N | 3-fluoro | 3-fluorophenyl | 639 |
| 68 | CH | N | 3-fluoro | pyridin-3-ylmethyl | 635 |
| 69 | CH | N | 3-fluoro | pyridin-4-ylmethyl | 635 |
| 70 | CH | N | 3-fluoro | quinolin-2-ylmethyl | 685 |
| 71 | CH | N | H | pyridin-2-ylmethyl | 617 |
| 72 | CH | N | H | pyridin-3-ylmethyl | 617 |
| 73 | CH | N | H | pyridin-4-ylmethyl | 617 |
| 74 | CH | N | H | quinolin-2-ylmethyl | 667 |
| 75 | CH | N | H | quinolin-4-ylmethyl | 667 |
| 76 | CH | N | H | 2-imidazolylmethyl | 605 |
| 77 | CH | N | H | (1-methyl-2-imidazolyl)methyl | 620 |
| 78 | CH | N | H | 2-pyrrolylmethyl | 605 |
| 79 | CH | N | H | (1-methyl-2-pyrrolyl)methyl | 619 |
| 80 | CH | N | H | 2-thiazolylmethyl | 623 |
| 81 | CH | N | H | 4-chlorophenylmethyl | 650 |
| 82 | CH | N | H | 3-chlorophenylmethyl | 650 |
| 83 | CH | N | H | 2-chlorophenylmethyl | 650 |
| 84 | CH | N | H | 4-fluorophenylmethyl | 634 |
| 85 | CH | N | H | 4-methoxyphenylmethyl | 646 |
| 86 | CH | N | H | Hydrogen | 526 |
| 87 | CH | N | H | Hydrogen | 543 |
| 88 | CH | N | H | methyl | 540 |
| 89 | CH | N | H | acetyl | 568 |
| 90 | CH | N | H | cyclohexylaminocarbonyl | 651 |
| 91 | CH | N | 3-fluoro | methanesulphonyl | 622 |
| 92 | CH | N | 3-fluoro | ethanesulphonyl | 635 |
| 93 | CH | N | 3-fluoro | isopropylsulphonyl | 650 |
| 94 | CH | N | 3-fluoro | benzenesulphonyl | 684 |
| 95 | CH | N | 3-fluoro | 4-methanesulphonylbenzenesulphonyl | 762 |
| 96 | CH | N | 3-fluoro | 4-chlorobenzoyl | 682 |
| 97 | CH | N | 3-fluoro | 4-methoxyphenylmethylaminocarbonyl | 707 |
| 98 | CH | N | 3-fluoro | cyclohexylaminocarbonyl | 668 |
| 99 | CH | N | 3-fluoro | phenylaminocarbonyl | 663 |
| 100 | CH | N | 3-fluoro | phenylmethylaminocarbonyl | 677 |
| 101 | CH | N | 3-fluoro | (4-sulphonamidophenyl)methylcarbonyl | 741 |
| 102 | CH | N | 3-fluoro | pyran-4-ylcarbonyl | 656 |
| 103 | CH | N | H | 4-fluorobenzoyl | 648 |
| 104 | CH | N | H | 3-fluorobenzoyl | 648 |
| 105 | CH | N | H | 2-fluorobenzoyl | 648 |
| 106 | CH | N | H | 2-chlorobenzoyl | 664 |
| 107 | CH | N | H | 3-chlorobenzoyl | 664 |
| 108 | CH | N | H | 2-methylbenzoyl | 644 |
| 109 | CH | N | H | 3-methylbenzoyl | 644 |
| 110 | CH | N | H | 4-methylbenzoyl | 644 |
| 111 | CH | N | H | cyclopentylcarbonyl | 622 |
| 112 | CH | N | H | propionyl | 582 |
| 113 | CH | N | H | cyclopropylcarbonyl | 594 |
| 114 | CH | N | H | pyrazin-2-ylcarbonyl | 632 |

TABLE I-continued

Table I comprises compounds of formula (Ib).

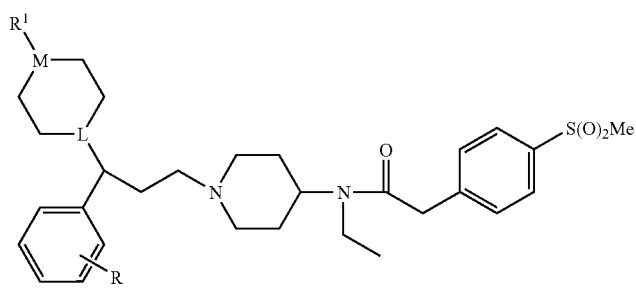

(Ib)

| Compound No. | L | M | R | R¹ | LCMS (MH+) |
|---|---|---|---|---|---|
| 115 | CH | N | H | 3-methanesulphonylbenzoyl | 708 |
| 116 | CH | N | H | (2-methylthiazol-4-yl)carbonyl | 651 |
| 117 | CH | N | H | methoxymethylcarbonyl | 598 |
| 118 | CH | N | H | 2,2,2-trifluoroethylcarbonyl | 636 |
| 119 | CH | N | H | 3-cyanophenylaminocarbonyl | 670 |
| 120 | CH | N | H | 3-fluorophenylaminocarbonyl | 663 |
| 121 | CH | N | H | 3-chlorophenylaminocarbonyl | 679 |
| 122 | CH | N | H | 3-methoxyphenylaminocarbonyl | 675 |
| 123 | CH | N | H | 2-methylphenylaminocarbonyl | 659 |
| 124 | CH | N | H | pyran-4-ylcarbonyl | 638 |
| 125 | CH | N | H | trifluoroacetyl | 622 |
| 126 | CH | N | H | 4-chlorophenylaminocarbonyl | 679 |
| 127 | CH | N | H | 4-fluorophenylaminocarbonyl | 663 |
| 128 | CH | N | H | 4-methoxyphenylaminocarbonyl | 675 |
| 129 | CH | N | H | 2,5-difluorophenylaminocarbonyl | 681 |
| 130 | CH | N | H | 3,4-dichlorophenylaminocarbonyl | 713 |
| 131 | CH | N | H | 2-methoxyphenylaminocarbonyl | 675 |
| 132 | CH | N | H | 2-chlorophenylaminocarbonyl | 279 |
| 133 | CH | N | H | trifluoromethanesulphonyl | 658 |
| 134 | N | N | H | 4-methanesulphonylbenzenesulphonyl | 745 |
| 135 | N | N | H | 4-cyanobenzenesulphonyl | 692 |
| 136 | N | N | H | 2-trifluoromethoxybenzenesulphonyl | |
| 137 | N | N | H | 3-chlorobenzenesulphonyl | 701 |
| 138 | N | N | H | 4-trifluoromethylbenzenesulphonyl | 735 |
| 139 | N | N | H | 4-trifluoromethoxybenzenesulphonyl | |
| 140 | N | N | H | 4-chlorobenzenesulphonyl | 701 |
| 141 | N | N | H | (3,5-dimethylisoxazolyl)sulphonyl | 686 |
| 142 | N | N | H | 2-thienylsulphonyl | 673 |
| 143 | N | N | H | (2-acetylamino-3-methyl)thiazol-5-ylsulphonyl | 745 |
| 144 | N | N | H | 4-acetylaminobenzenesulphonyl | 724 |
| 145 | CH | N | 3-fluoro | phenyl | 620 |
| 146 | CH | N | 3-fluoro | 4-methoxyphenyl | 650 |
| 147 | CH | N | 3-fluoro | 4-fluorophenyl | 638 |
| 148 | CH | N | H | 3-chlorophenyl | 654 |
| 149 | CH | N | H | 4-chlorophenyl | 654 |
| 150 | N | N | H | 2-chlorobenzenesulphonyl | 701 |
| 151 | N | N | H | 4-chlorobenzoyl | 665 |
| 152 | CH | N | H | tert-butoxycarbonyl | 626 |
| 153 | CH | N | 3-fluoro | tert-butoxycarbonyl | 612 |
| 154 | CH | N | H | 2,2,2-trifluoroethanesulphonyl | 672 |
| 155 | N | N | 4-fluoro | methanesulphonyl | 623 |
| 156 | N | N | 4-fluoro | 4-methanesulphonylbenzenesulphonyl | 763.3 |
| 157 | N | N | 3,4-difluoro | methanesulphonyl | 641.4 |
| 158 | N | N | 3-chloro | methanesulphonyl | 639 |

TABLE II

Table II comprises compounds of formula (Ic).

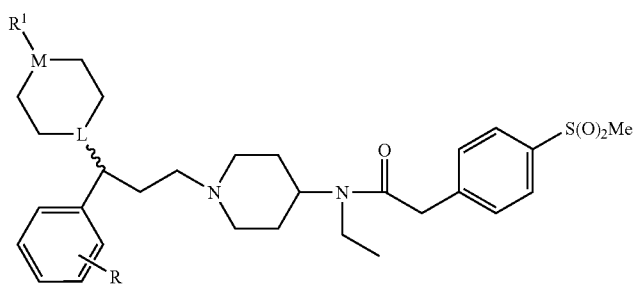

(Ic)

| Compound No. | L | M | R | Stereochem | R¹ | LCMS (MH+) |
|---|---|---|---|---|---|---|
| 1 | N | N | H | R or S | benzenesulphonyl | 667 |
| 2 | N | N | H | S or R | 4-methanesulphonylbenzenesulphonyl | 745 |
| 3 | N | N | H | S or R | 3-methylphenyl | 617 |
| 4 | N | N | H | S orR | 4-methylphenyl | 617 |
| 5 | N | N | H | S or R | 2-methylphenyl | 617 |
| 6 | N | N | H | S or R | 2-methoxyphenyl | 633 |
| 7 | N | N | H | S or R | 3-methoxyphenyl | 633 |
| 8 | N | N | H | S or R | 2,6-dimethylphenyl | 631 |
| 9 | N | N | H | S or R | 2-cyanophenyl | 628 |
| 10 | N | N | H | S or R | 2-nitrophenyl | 648 |
| 11 | N | N | H | S or R | 2-methylthiophenyl | 649 |
| 12 | N | N | H | S or R | 4-fluorophenyl | 621 |
| 13 | N | N | H | S or R | 2,6-dichlorophenyl | 672 |
| 14 | N | N | H | S or R | n-propanesulphonyl | 633 |
| 15 | N | N | H | S or R | 2,2,2-trifluoroethanesulphonyl | 673 |
| 16 | N | N | 3-fluoro | S or R | 4-methanesulphonylbenzenesulphonyl | |
| 17 | N | N | 3-fluoro | R or S | 4-methanesulphonylbenzenesulphonyl | |
| 18 | CH | N | H | R | ethanesulphonyl | 654 |
| 19 | CH | N | H | S | ethanesulphonyl | 654 |
| 20 | CH | N | H | R | methanesulphonyl | 604 |
| 21 | CH | N | H | S | methanesulphonyl | 604 |
| 22 | CH | N | 3-fluoro | R | ethanesulphonyl | 636 |
| 23 | CH | N | 3-fluoro | S | ethanesulphonyl | 636 |
| 24 | CH | N | H | R | benzyloxycarbonyl | 659 |
| 25 | CH | N | H | R | phenylaminocarbonyl | |
| 26 | CH | N | H | R | 4-chlorobenzoyl | |
| 27 | CH | N | H | R | 4-methanesulphonylbenzenesulphonyl | |
| 28 | CH | N | 3-fluoro | R | 4-chlorobenzoyl | |
| 29 | CH | N | 3-fluoro | S | 4-chlorobenzoyl | |
| 30 | CH | N | 3-fluoro | R | 4-methanesulphonylbenzenesulphonyl | |
| 31 | CH | N | 3-fluoro | S | 4-methanesulphonylbenzenesulphonyl | |
| 32 | CH | N | 3,5-difluoro | R | trifluoromethanesulphonyl | 694 |
| 33 | CH | N | H | R | 4-fluorobenzoyl | 648 |
| 34 | CH | N | H | S | 4-fluorobenzoyl | 648 |
| 35 | CH | N | H | R | hydrogen | 526 |
| 36 | CH | N | H | R | trifluoromethanesulphonyl | 658 |
| 37 | CH | N | H | S | trifluoromethanesulphonyl | 658 |
| 38 | CH | N | 2-methylthio | R | methanesulphonyl | 650 |
| 39 | CH | N | H | R | N,N-dimethylaminosulphonyl | 633 |

TABLE III

Table III comprises compounds of formula (Id).

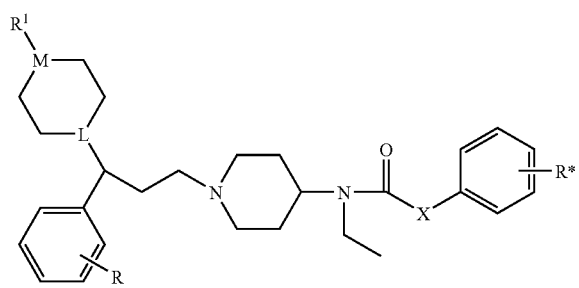

(Id)

| Compound No. | L | M | X | R | R* | R¹ | LCMS (MH+) |
|---|---|---|---|---|---|---|---|
| 1 | N | N | NHCH₂ | H | 4-methanesulphonyl | benzenesulphonyl | 682 |
| 2 | N | N | NHCH₂ | H | 4-methanesulphonyl | benzoyl | 646 |
| 3 | N | N | NHCH₂ | H | 4-methanesulphonyl | ethanesulphonyl | 634 |
| 4 | N | N | NHCH₂ | H | 4-methanesulphonyl | methanesulphonyl | 620 |
| 5 | N | N | NHCH₂ | H | 4-methanesulphonyl | 4-chlorobenzoyl | 680 |
| 6 | CH | N | NHCH₂ | H | 4-methanesulphonyl | benzenesulphonyl | 681 |
| 7 | CH | N | NHCH₂ | H | 4-methanesulphonyl | ethanesulphonyl | 633 |
| 8 | CH | N | NHCH₂ | H | 4-methanesulphonyl | hydrogen | 541 |
| 9 | CH | N | NHCH₂ | H | 4-methanesulphonyl | methanesulphonyl | 619 |
| 10 | CH | N | NHCH₂ | H | 4-methanesulphonyl | 4-methanesulphonylbenzenesulphonyl | |
| 11 | CH | N | NHCH₂ | H | 4-methanesulphonyl | phenylmethylcarbonyl | 659 |
| 12 | CH | N | NHCH₂ | H | 4-methanesulphonyl | 4-chlorobenzoyl | 679 |
| 13 | CH | N | NHCH₂ | H | 4-methanesulphonyl | cyclohexylaminocarbonyl | 666 |
| 14 | CH | N | NHCH₂ | H | 4-methanesulphonyl | 4-fluorophenylmethylaminocarbonyl | 692 |
| 15 | CH | N | NHCH₂ | H | 4-methanesulphonyl | 4-methanesulphonylbenzoyl | 723 |
| 16 | CH | N | NHCH₂ | H | 4-methanesulphonyl | pyridin-2-ylmethylcarbonyl | 660 |
| 17 | CH | N | NHCH₂ | H | 4-methanesulphonyl | pyridin-3-ylmethylcarbonyl | 660 |
| 18 | CH | N | NHCH₂ | H | hydrogen | ethanesulphonyl | 555 |
| 19 | CH | N | NHCH₂ | H | 4-methoxy | ethanesulphonyl | 585 |
| 20 | CH | N | NHCH₂ | H | 4-fluoro | ethanesulphonyl | 573 |
| 21 | CH | N | NHCH₂ | H | 3-methyl | ethanesulphonyl | 569 |
| 22 | CH | N | NHCH₂ | H | 3-methoxy | ethanesulphonyl | 571 |
| 23 | CH | N | NH | H | 3-chloro | ethanesulphonyl | 574 |
| 24 | CH | N | NH | H | 2-methyl | ethanesulphonyl | 554 |
| 25 | CH | N | NH | H | 4-bromo | ethanesulphonyl | 621 |
| 26 | CH | N | NH | H | 3-cyano | ethanesulphonyl | 566 |
| 27 | CH | N | NHCH₂ | H | hydrogen | benzensulphonyl | 603 |
| 28 | CH | N | NHCH₂ | H | 4-methoxy | benzenesulphonyl | 633 |
| 29 | CH | N | NHCH₂ | H | 4-fluoro | benzenesulphonyl | 621 |
| 30 | CH | N | NHCH₂ | H | 3-methyl | benzenesulphonyl | 616 |
| 31 | CH | N | NH | H | 3-fluoro | benzenesulphonyl | 607 |
| 32 | CH | N | NH | H | 3-methoxy | benzenesulphonyl | 619 |
| 33 | CH | N | NH | H | 3-chloro | benzenesulphonyl | 623 |
| 34 | CH | N | NH | H | 2-methyl | benzenesulphonyl | 603 |
| 35 | CH | N | NH | H | 4-bromo | benzenesulphonyl | 669 |
| 36 | CH | N | NH | H | 3-cyano | benzenesulphonyl | 614 |
| 37 | CH | N | CH₂ | 3-fluoro | 4-sulphonamido | tert-butyloxycarbonyl | 645 |
| 38 | CH | N | CH₂ | 3-fluoro | 4-sulphonamido | hydrogen | 545 |
| 39 | CH | N | CH₂ | 3-fluoro | 4-sulphonamido | 4-methanesulphonylbenzenesulphonyl | 763 |
| 40 | CH | N | CH₂ | 3-fluoro | 4-sulphonamido | cyclohexylaminocarbonyl | 670 |
| 41 | CH | N | CH₂ | 3-fluoro | 4-sulphonamido | methanesulphonyl | 623 |
| 42 | CH | N | CH₂ | 3-fluoro | 4-sulphonamido | ethanesulphonyl | 637 |
| 43 | CH | N | NHCH₂ | H | 4-methanesulphonyl | 1-methylethanesulphonyl | 647 |

TABLE IV

Table IV comprises compounds of formula (Ie).

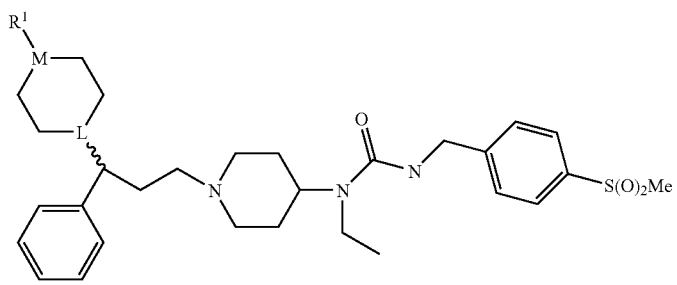

(Ie)

| Compound No. | L | M | Stereochem | R¹ | LCMS (MH+) |
|---|---|---|---|---|---|
| 1 | N | N | S or R | benzenesulphonyl | 682 |
| 2 | N | N | S or R | ethanesulphonyl | 634 |
| 3 | N | N | S or R | methanesulphonyl | 620 |
| 4 | CH | N | R | methanesulphonyl | 650 |

TABLE V

Table V comprises compounds of formula (If).

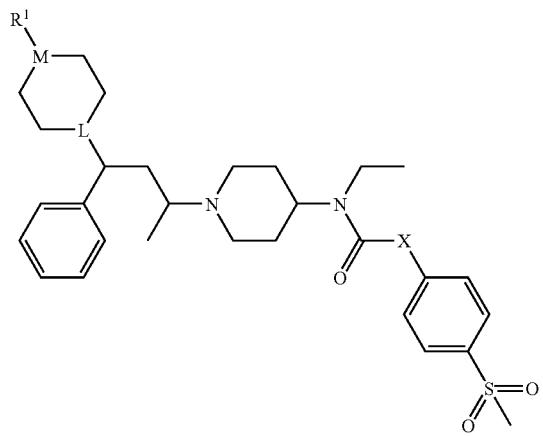

(If)

| Compound No. | L | M | X | R¹ | LCMS (MH+) |
|---|---|---|---|---|---|
| 1 | N | N | $CH_2$ | benzenesulphonyl | 681 |
| 2 | N | N | $NHCH_2$ | benzenesulphonyl | 696 |
| 3 | N | N | $NHCH_2$ | methanesulphonyl | 634 |

TABLE VI

Table VI comprises compounds of formula (Ig).

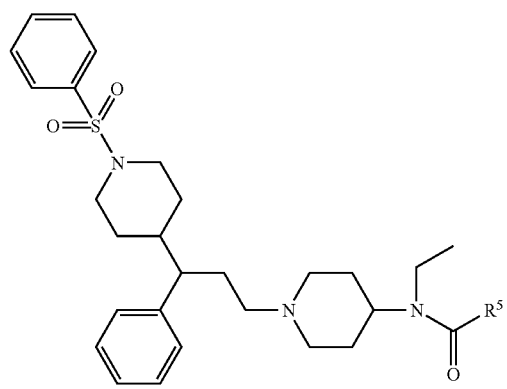

(Ig)

| Compound No | R⁵ | LCMS (MH⁺) |
|---|---|---|
| 1 | pyridin-2-yl$CH_2$ | 589 |
| 2 | pyridin-3-yl$CH_2$ | 589 |
| 3 | pyridin-4-yl$CH_2$ | 589 |

In yet another aspect the invention provides each individual compound listed in the tables above.

The compounds of formula (I), (Ia), (Ib), (Ic), (Id), (Ie), (If) and (Ig) can be prepared as shown below (for example in Schemes 2 and 3, with Scheme 1 showing the preparation of an intermediate.) In Schemes 1 to 3: PG is a protecting Group; Ac is acetyl; Boc is tert-butoxycarbonyl; Bn is benzyl, Bz is benzoyl; DIBAL is diisobutylaluminium hydride; Et is ethyl; Ms is mesyl; and, TFA is trifluoroacetic acid.

A compound of the invention wherein L is N can be prepared by reacting a compound of formula (II):

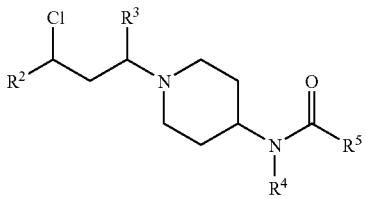

(II)

wherein $R^2$, $R^3$, $R^4$ and $R^5$ are as defined above, with a compound of formula (III):

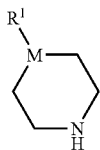

(III)

wherein $R^1$ is as defined above, in the presence of sodium iodide rand a suitable base (for example a tri($C_{1-6}$ alkyl) amine such as triethylamine or Hunig's base), in a suitable solvent (such as a chlorinated solvent, for example dichloromethane) and, for example, at a room temperature (for example 10–30° C.).

A compound of the invention wherein L is CH can be prepared by reacting a compound of formula (IV):

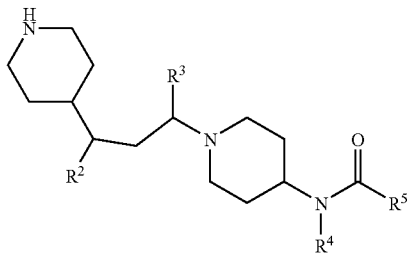

(IV)

wherein $R^2$, $R^3$, $R^4$ and $R^5$ are as defined above, with, depending on the compound of the invention it is desired to make:

a) an acid of formula $R^1CO_2H$ in the presence of a suitable coupling agent (for example PyBrOP [bromo-tris-pyrrolidino-phosphonium hexafluorophosphate] or HATU) in the presence of a suitable base (such as a tri($C_{1-6}$ alkylamine, for example diisopropylethylamine) in a suitable solvent (for example N-methylpyrrolidinone or a chlorinated solvent, such as dichloromethane) at room temperature (for example 10–30° C.);

b) an acid chloride of formula $R^1C(O)Cl$ or sulphonyl chloride of formula $R^1S(O)_2Cl$, in the presence of a suitable base (such as a tri($C_{1-6}$ alkyl)amine, for example triethylamine or diisopropylethylamine) in a suitable solvent (for example a chlorinated solvent, such as dichloromethane) at room temperature (for example 10–30° C.); or, c) an aldehyde of formula $R^1CHO$ in the presence of $NaBH(OAc)_3$ (wherein Ac is $C(O)CH_3$) and acetic acid, in a suitable solvent (such as a $C_{1-6}$ aliphatic alcohol, for example ethanol) at room temperature (for example 10–30° C.).

Alternatively, a compound of the invention can be prepared by coupling a compound of formula (V):

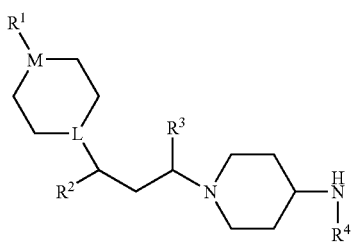

(V)

wherein L, M, $R^1$, $R^2$, $R^3$ and $R^4$ are as defined above, with:

a) an acid of formula $R^5CO_2H$ in the presence of a suitable coupling agent (for example PyBrOP or HATU) in the presence of a suitable base (such as a tri($C_{1-6}$ alkyl)amine, for example diisopropylethylamine) in a suitable solvent (for example N-methylpyrrolidinone or a chlorinated solvent, such as dichloromethane) at room temperature (for example 10–30° C.); or, b) an acid chloride of formula $R^5C(O)Cl$, in the presence of a suitable base (such as a tri($C_{1-6}$ alkyl)amine, for example triethylamine or diisopropylethylamine) in a suitable solvent (for example a chlorinated solvent, such as dichloromethane) at room temperature (for example 10–30° C.).

The starting materials for these processes are either commercially available or can be prepared by literature methods, adapting literature methods or by following or adapting Methods herein described.

In a further aspect the invention provides an intermediate of formula (V).

In a still further aspect the invention provides processes for preparing the compounds of formula (I), (Ia), (Ib), (Ic), (Id), (Ie), (If) and (Ig). Many of the intermediates in the processes are novel and these are provided as further features of the invention.

The compounds of the invention have activity as pharmaceuticals, in particular as modulators (such as agonists, partial agonists, inverse agonists or antagonists) of chemokine receptor (especially CCR5) activity, and may be used in the treatment of autoimmune, inflammatory, proliferative or hyperproliferative diseases, or immunologically-mediated diseases (including rejection of transplanted organs or tissues and Acquired Immunodeficiency Syndrome (AIDS)).

The compounds of the present invention are also of value in inhibiting the entry of viruses (such as human immunodeficiency virus (HIV)) into target calls and, therefore, are of value in the prevention of infection by viruses (such as HIV), the treatment of infection by viruses (such as HIV) and the prevention and/or treatment of acquired immune deficiency syndrome (AIDS).

According to a further feature of the invention there is provided a compound of the formula (I), (Ia), (Ib), (Ic), (Id), (Ie), (If) or (Ig) (such as (I) or (Ia)), or a pharmaceutically acceptable salt thereof or a solvate thereof, for use in a method of treatment of a warm blooded animal (such as man) by therapy (including prophylaxis).

According to a further feature of the present invention there is provided a method for modulating chemokine receptor activity (especially CCR5 receptor activity) in a warm blooded animal, such as man, in need of such treatment, which comprises administering to said animal an effective amount of a compound of the present invention, or a pharmaceutically acceptable salt thereof or a solvate thereof.

The present invention also provides the use of a compound of the formula (I), (Ia), (Ib), (Ic), (Id), (Ie), (If) or (Ig) (such as (I) or (Ia)), or a pharmaceutically acceptable salt thereof or a solvate thereof, as a medicament, especially a medicament for the treatment of transplant rejection, respiratory disease, psoriasis or rheumatoid arthritis (especially rheumatoid arthritis). [Respiratory disease is, for example, COPD, asthma {such as bronchial, allergic, intrinsic, extrinsic or dust asthma, particularly chronic or inveterate asthma (for example late asthma or airways hyper-responsiveness)} or rhinitis {acute, allergic, atrophic rhinitis or chronic rhinitis including rhinitis caseosa, hypertrophic rhinitis, rhinitis purulenta, rhinitis sicca or rhinitis medicamentosa; membranous rhinitis including croupous, fibrinous or pseudomembranous rhinitis or scrofoulous rhinitis; seasonal rhinitis including rhinitis nervosa (hay fever) or vasomotor rhinitis}; and is particularly asthma or rhinitis].

In another aspect the present invention provides the use of a compound of the formula (I), (Ia), (Ib), (Ic), (Id), (Ie), (If) or (Ig) (such as (I) or (Ia)), or a pharmaceutically acceptable salt thereof or a solvate thereof, in the manufacture of a medicament for use in therapy (for example modulating chemokine receptor activity (especially CCR5 receptor activity (especially rheumatoid arthritis)) in a warm blooded animal, such as man).

The invention also provides a compound of the formula (I), (Ia), (Ib), (Ic), (Id), (Ie), (If) or (Ig) (such as (I) or (Ia)), or a pharmaceutically acceptable salt thereof or a solvate thereof, for use as a medicament, especially a medicament for the treatment of rheumatoid arthritis.

In another aspect the present invention provides the use of a compound of the formula (I), (Ia), (Ib), (Ic), (Id), (Ie), (If) or (Ig) (such as (I) or (Ia)), or a pharmaceutically acceptable salt thereof or a solvate thereof, in the manufacture of a medicament for use in therapy (for example modulating chemokine receptor activity (especially CCR5 receptor activity (especially rheumatoid arthritis)) in a warmblooded animal, such as man).

The invention further provides the use of a compound of formula (I), (Ia), (Ib), (Ic), (Id), (Ie), (If) or (Ig) (such as (I) or (Ia)), or a pharmaceutically acceptable salt thereof, in the manufacture of a medicament for use in the treatment of:

(1) (the respiratory tract) obstructive diseases of airways including: chronic obstructive pulmonary disease (COPD) (such as irreversible COPD); asthma {.such as bronchial, allergic, intrinsic, extrinsic or dust asthma, particularly chronic or inveterate asthma (for example late asthma or airways hyper-responsiveness)}; bronchitis {such as eosinophilic bronchitis}; acute, allergic, atrophic rhinitis or chronic rhinitis including rhinitis caseosa, hypertrophic rhinitis, rhinitis purulenta, rhinitis sicca or rhinitis medicamentosa; membranous rhinitis including croupous, fibrinous or pseudomembranous rhinitis or scrofoulous rhinitis; seasonal rhinitis including rhinitis nervosa (hay fever) or vasomotor rhinitis; sarcoidosis; farmer's lung and related diseases; nasal polyposis; fibroid lung or idiopathic interstitial pneumonia;

(2) (bone and joints) arthrides including rheumatic, infectious, autoimmune, seronegative spondyloarthropathies (such as ankylosing spondylitis, psoriatic arthritis or Reiter's disease), Behcet's disease, Sjogren's syndrome or systemic sclerosis;

(3) (skin and eyes) psoriasis, atopic dermatitis, contact dermatitis or other eczmatous dermitides, seborrhoetic dermatitis, Lichen planus, Phemphigus, bullous Phemphigus, Epidermolysis bullosa, urticaria, angiodermas, vasculitides erythemas, cutaneous eosinophilias, uveitis, Alopecia areata or vernal conjunctivitis;

(4) (gastrointestinal tract) Coeliac disease, proctitis, eosinophilic gastro-enteritis, mastocytosis, Crohn's disease, ulcerative colitis, irritable bowel disease or food-related allergies which have effects remote from the gut (for example migraine, rhinitis or eczema);

(5) (Allograft rejection) acute and chronic following, for example, transplantation of kidney, heart, liver, lung, bone marrow, skin or cornea; or chronic graft versus host disease; and/or (6) (other tissues or diseases) Alzheimer's disease, multiple sclerosis, atherosclerosis, Acquired Immunodeficiency Syndrome (AIDS), Lupus disorders (such as lupus erythematosus or systemic lupus), erythematosus, Hashimoto's thyroiditis, myasthenia gravis, type I diabetes, nephrotic syndrome, eosinophilia fascitis, hyper IgE syndrome, leprosy (such as lepromatous leprosy), Peridontal disease, Sezary syndrome, idiopathic thrombocytopenia pupura or disorders of the menstrual cycle;

in a warm blooded animal, such as man.

The present invention further provides a method of treating a chemokine mediated disease state (especially a CCR5 mediated disease state) in a warm blooded animal, such as man, which comprises administering to a mammal in need of such treatment an effective amount of a compound of formula (I), (Ia), (Ib), (Ic), (Id), (Ie), (If) or (Ig) (such as (I) or (Ia)), or a pharmaceutically acceptable salt thereof or solvate thereof.

In order to use a compound of the invention, or a pharmaceutically acceptable salt thereof or solvate thereof, for the therapeutic treatment of a warm blooded animal, such as man, in particular modulating chemokine receptor (for example CCR5 receptor) activity, said ingredient is normally formulated in accordance with standard pharmaceutical practice as a pharmaceutical composition.

Therefore in another aspect the present invention provides a pharmaceutical composition which comprises a compound of the formula (I), (Ia), (Ib), (Ic), (Id), (Ie), (If) or (Ig) (such as (I) or (Ia)), or a pharmaceutically acceptable salt thereof or a solvate thereof (active ingredient), and a pharmaceutically acceptable adjuvant, diluent or carrier. In a further aspect the present invention provides a process for the preparation of said composition which comprises mixing active ingredient with a pharmaceutically acceptable adjuvant, diluent or carrier. Depending on the mode of administration, the pharmaceutical composition will preferably comprise from 0.05 to 99% w (per cent by weight), more preferably from 0.05 to 80% w, still more preferably from 0.10 to 70% w, and even more preferably from 0.10 to 50% w, of active ingredient, all percentages by weight being based on total composition.

The pharmaceutical compositions of this invention may be administered in standard manner for the disease condition that it is desired to treat, for example by topical (such as to the lung and/or airways or to the skin), oral, rectal or parenteral administration. For these purposes the compounds of this invention may be formulated by means known in the art into the form of, for example, aerosols, dry powder formulations, tablets, capsules, syrups, powders, granules, aqueous or oily solutions or suspensions, (lipid) emulsions, dispersible powders, suppositories, ointments, creams, drops and sterile injectable aqueous or oily solutions or suspensions.

A suitable pharmaceutical composition of this invention is one suitable for oral administration in unit dosage form, for example a tablet or capsule which contains between 0.1 mg and 1 g of active ingredient.

In another aspect a pharmaceutical composition of the invention is one suitable for intravenous, subcutaneous or intramuscular injection.

Each patient may receive, for example, an intravenous, subcutaneous or intramuscular dose of 0.01 $mgkg^{-1}$ to 100 $mgkg^{-1}$ of the compound, preferably in the range of 0.1 $mgkg^{-1}$ to 20 $mgkg^{-1}$ of this invention, the composition being administered 1 to 4 times per day. The intravenous, subcutaneous and intramuscular dose may be given by means of a bolus injection. Alternatively the intravenous dose may be given by continuous infusion over a period of time. Alternatively each patient will receive a daily oral dose which is approximately equivalent to the daily parenteral dose, the composition being administered 1 to 4 times per day.

The following illustrate representative pharmaceutical dosage forms containing the compound of formula (I), (Ia), (Ib), (Ic), (Id), (Ie), (If or (Ig) (such as (I) or (Ia)), or a pharmaceutically acceptable salt thereof or a solvent thereof (hereafter Compound X), for therapeutic or prophylactic use in humans:

| (a) | |
|---|---|
| Tablet I | mg/tablet |
| Compound X | 100 |
| Lactose Ph.Eur. | 179 |
| Croscarmellose sodium | 12.0 |
| Polyvinylpyrrolidone | 6 |
| Magnesium stearate | 3.0 |

| (b) | |
|---|---|
| Tablet II | mg/tablet |
| Compound X | 50 |
| Lactose Ph.Eur. | 229 |
| Croscarmellose sodium | 12.0 |
| Polyvinylpyrrolidone | 6 |
| Magnesium stearate | 3.0 |

| (c) | |
|---|---|
| Tablet III | mg/tablet |
| Compound X | 1.0 |
| Lactose Ph.Eur. | 92 |
| Croscarmellose sodium | 4.0 |
| Polyvinylpyrrolidone | 2.0 |
| Magnesium stearate | 1.0 |

| (d) | |
|---|---|
| Capsule | mg/capsule |
| Compound X | 10 |
| Lactose Ph.Eur. | 389 |
| Croscarmellose sodium | 100 |
| Magnesium stearate | 1.0 |

| (e) | |
|---|---|
| Injection I | (50 mg/ml) |
| Compound X | 5.0% w/v |
| Isotonic aqueous solution | to 100% |

Buffers, pharmaceutically-acceptable cosolvents such as polyethylene glycol, polypropylene glycol, glycerol or ethanol or complexing agents such as hydroxy-propyl β-cyclodextrin may be used to aid formulation.

The above formulations may be obtained by conventional procedures well known in the pharmaceutical art. The tablets (a)–(c) may be enteric coated by conventional means, for example to provide a coating of cellulose acetate phthalate.

The invention will now be illustrated by the following non-limiting Examples in which, unless stated otherwise:

(i) temperatures are given in degrees Celsius (° C.); operations were carried out at room or ambient temperature, that is, at a temperature in the range of 18–25° C.;

(ii) organic solutions were dried over anhydrous magnesium sulfate; evaporation of solvent was carried out using a rotary evaporator under reduced pressure (600–4000 Pascals; 4.5–30 mm Hg) with a bath temperature of up to 60° C.;

(iii) chromatography unless otherwise stated means flash chromatography on silica gel; thin layer chromatography (TLC) was carried out on silica gel plates; where a "Bond Elut" column is referred to, this means a column containing 10 g or 20 g of silica of 40 micron particle size, the silica being contained in a 60 ml disposable syringe and supported by a porous disc, obtained from Varian, Harbor City, Calif., USA under the name "Mega Bond Elut SI". Where an "Isolute™ SCX column" is referred to, this means a column containing benzenesulphonic acid (non-endcapped) obtained from International Sorbent Technology Ltd., 1st House, Duffryn Industial Estate, Ystrad Mynach, Hengoed, Mid Glamorgan, UK. Where "Argonaut™ PS-tris-amine scavenger resin" is referred to, this means a tris-(2-aminoethyl)amine polystyrene resin obtained from Argonaut Technologies Inc., 887 Industrial Road, Suite G, San Carlos, Calif., USA.

(iv) in general, the course of reactions was followed by TLC and reaction times are given for illustration only;

(v) yields, when given, are for illustration only and are not necessarily those which can be obtained by diligent process development; preparations were repeated if more material was required;

(vi) when given, $^1$H NMR data is quoted and is in the form of delta values for major diagnostic protons, given in parts per million (ppm) relative to tetramethylsilane (TMS) as an internal standard, determined at 300 MHz using perdeuterio DMSO ($CD_3SOCD_3$) as the solvent unless otherwise stated; coupling constants (J) are given in Hz;

(vii) chemical symbols have their usual meanings; SI units and symbols are used;

(viii) solvent ratios are given in percentage by volume;

(ix) mass spectra (MS) were run with an electron energy of 70 electron volts in the chemical ionisation (APCI) mode using a direct exposure probe; where indicated ionisation was effected by electrospray (ES); where values for m/z are given, generally only ions which indicate the parent mass are reported, and unless otherwise stated the mass ion quoted is the positive mass ion—(M+H)$^+$;

(x) LCMS characterisation was performed using a pair of Gilson 306 pumps with Gilson 233 XL sampler and Waters ZMD4000 mass spectrometer. The LC comprised water symmetry 4.6×50column C18 with 5 micron particle size. The eluents were: A, water with 0.05% formic acid and B, acetonitrile with 0.05% formic acid. The eluent gradient went from 95% A to 95% B in 6 minutes. Where indicated ionisation was effected by electrospray (ES); where values for m/z are given, generally only ions which indicate the parent mass are reported, and unless otherwise stated the mass ion quoted is the positive mass ion—(M+H)$^+$ and (xi) the following abbreviations are used:

| | |
|---|---|
| DMSO | dimethyl sulfoxide; |
| DMF | N-dimethylformamide; |
| DCM | dichloromethane; |
| THF | tetrahydrofuran; |
| DIPEA | N,N-diisopropylethylamine; |
| NMP | N-methylpyrrolidinone; |
| HATU | O-(7-Azabenzotriazol-1-yl)-N,N,N',N'-tetramethyluronium hexafluorophosphate; |
| HBTU | O-(7-Benzotriazol-1-yl)-N,N,N',N'-tetramethyluronium hexafluorophosphate; |
| Boc | tert-butoxycarbonyl |
| MeOH | methanol; |
| EtOH | ethanol; and |
| EtOAc | ethyl acetate. |

EXAMPLE 1

This Example illustrates the preparation of N-[1-(3-phenyl-3-[4-methylpiperazin-1-yl]propyl)-piperidin-4yl]-N-ethyl-4-methanesulfonylphenylacetamide (Compound No. 6 of Table I).

To a solution of 1-methylpiperazine (42 µL, 0.38 mmol) in DCM (10 mL) was added triethylamine (0.1 mL, 0.72 mmol) then N-[1-(3-phenyl-3-chloropropyl)-piperidin-4-yl]-N-ethyl-4-methanesulfonylphenylacetamide (Method A; 180 mg, 0.38 mmol) and sodium iodide (50 mg). The resulting mixture was stirred at room temperature for 48 h then washed with water and brine, dried (MgSO$_4$) and evaporated. The residue was purified by eluting through a 20 g Bond Elut with 10% methanol in ethyl acetate then methanol then 1% triethylanine in methanol to give the title compound (58mg); NMR : 1.2 (t, 1H), 1.3 (t, 2H), 1.4 (m, 1H), 1.6 (m, 2H), 1.8 (m, 4H), 1.9 (m,2 H), 2.1 (m, 2H), 2.2 (s, 3H), 2.4 (m, 8H), 2.9 (m, 2H), 3.0 (s, 3H), 3.3 (m, 2H), 3.8 (s, 2H), 7.2 (m, 2H), 7.4 (m, 2H), 7.9 (d, 2H); MS: 541.

The procedure described in Example 1 can be repeated using different secondary amines (such as 4-formylpiperazine, 4-isobutyrylpiperazine or 4-benzylpiperidine) in place of 1-methylpiperazine.

EXAMPLE 2

This Example illustrates the preparation of N-[1-(3-phenyl-3-[piperidin-4-yl]propyl)-piperidin-4-yl]-N-ethyl-4-methanesulfonylphenylacetamide (Compound No. 17 of Table I).

N-[1-(3-Phenyl-3-[1-tert-butylcarbonyloxypiperidin-4-yl]propyl)-piperidin-4-yl]-N-ethyl-4-methanesulfonylphenylacetamide (Example 3, 4 g) was dissolved in trifluoroacetic acid (25 mL) and the resulting mixture was stirred at room temperature for 2 h. The mixture was evaporated and the residue azeotroped with toluene. The resulting material was stirred with 2M aqueous sodium hydroxide (25 mL) and the resulting mixture extracted with DCM (8×25 mL). The combined extracts were dried and evaporated to give the tide compound (2.5 g); MS: 526.

EXAMPLE 3

This Example illustrates the preparation of N-[1-(3-phenyl-3-[1-tert-butylcarbonyloxy-piperidin-4-yl]propyl)-piperidin-4-yl]-Nethyl-4-methanesulfonylphenylacetamide (Compound No. 23 of Table I).

To a solution of 3-phenyl-3-(1-tert-butylcarbonyloxypiperidin-4-yl)propionaldehyde (Method C; 14.4 mmol) in DCM (100 mL) was added N-(4-piperidinyl)-N-ethyl-4-methanesulfonylphenylacetamide (Method B; 4.6 g, 14.4 mmol) and the resulting mixture was stirred at room temperature for 30 min. Sodium triacetoxyborohydride (3.05 g, 14.4 mmol) was added and the resulting mixture was stirred at room temperature for 2 h. The reaction mixture was washed with 2M aqueous sodium hydroxide (3×25 mL), dried and eluted through a 50 g SCX cartridge with DCM (3×25 mL), ethyl acetate (4×25 mL), methanol (4×25 mL) and finally 1M ammonia in methanol (4×50 mL) to yield crude product which was purified by silica gel chromatography (eluent: ethyl acetate then 10% methanol in. ethyl acetate) to yield the title compound (4.2 g); MS: 626.

EXAMPLE 4

This Example illustrates the preparation of N-[1-(3-phenyl-3-[1-methylpiperidin-4-yl]propyl)-piperidin-4-yl]-N-ethyl-4-methanesulfonylphenylacetamide (Compound No. 26 of Table I).

To a mixture of N-[1-(3-phenyl-3-[piperidin-4-yl]propyl)-piperidin-4-yl]-N-ethyl-4-methanesulfonylphenylacetamide (Example 2, 250 mg, 4.76 mmol) and formaldehyde (0.2 mL, 37% aqueous) in DCM (10 mL) was added sodium triacetoxyborohydride (9.52 mmol) and the resulting mixture was stirred at room temperature for 18 h. The mixture was washed with 2M aqueous sodium hydroxide (10 mL) and eluted through a 10 g SCX cartridge with DCM (2×10 mL), methanol (2×10 mL) and finally 1M ammonia in methanol (4×10 mL) affording the title compound (172 mg); MS: 540.

The procedure described in Example 4 can be repeated using different aldehydes (such as acetaldehyde and benzaldehyde) in place of formaldehyde.

EXAMPLE 5

This Example illustrates the preparation of N-[1-(3-phenyl-3-[1-acetylpiperidin-4-yl]propyl)-piperidin-4-yl]-N-ethyl-4-methanesulfonylphenylacetamide (Compound No. 21 of Table I).

To a mixture of N-[1-(3-phenyl-3-[piperidin-4-yl]propyl)-piperidin-4-yl]-N-ethyl-4-methanesulfonylphenylacetamide (Example 2, 250 mg, 4.76 mmol) and triethylamine (48 mg, 4.76 mmol) in DCM was added acetyl chloride (37 mg, 4.76 mmol). The resulting mixture was stirred at room temperature for 18 h, washed with saturated aqueous sodium bicarbonate solution (10 mL), dried and eluted through a 10 g SCX cartridge with DCM (2×10 mL), methanol (4×10 mL) and finally 1M ammonia in methanol (4×10 mL) affording the title compound (180 mg); MS: 568.

The procedure described in Example 5 can be repeated using different acid chlorides (such as phenylacetyl chloride and 4-chlorobenzoyl chloride) or sulfonyl chlorides (such as methane sulfonyl chloride) in place of acetyl chloride.

EXAMPLE 6

This Example illustrates the preparation of N-[1-(3-phenyl-3-[1-cyclohexylamino-carbonylpiperidin-4-yl]propyl)-piperidinyl]-N-ethyl-4-methanesulfonylphenylacetamide (Compound No. 22 of Table I).

To a mixture of N-[1-(3-phenyl-3-[piperidin-4yl]propyl)-piperidin-4-yl]-N-ethyl-4-methanesulfonylphenylacetamide (Example 2, 250 mg, 4.76 mmol) and DCM (10 mL) was added cyclohexyl isocyanate (59 mg, 4.6 mmol) and the resulting mixture was stirred at room temperature for 18 h. The mixture was eluted through a 10 g SCX cartridge with DCM (4×10 mL), methanol (2×10 mL) and finally 1M ammonia in methanol (4×10 mL) affording the title compound (300 mg); MS: 651.

EXAMPLE 7

N-[1-(3-phenyl-3-[4-(2-chlorophenylsulphonyl)piperazin-1-yl]propyl)-piperidin-4-yl]-N-ethyl-4-methanesulphonylphenylacetamide (Compound Number 150 of Table 1)

2-Chlorophenylsulphonyl chloride (40.1 mg) was added to a solution of N-[1-(3-phenyl-3-[piperazin-1-yl]propyl)-piperidin-4-yl]-N yl-4-methanesulphonylphenyl-acetamide (100 mg) and triethylamine (53 µl) in dichloromethane (5 ml) and the mixture was stirred for 1 hour. The reaction mixture was washed with water, brine and dried. The solvent was removed and the residue was chromatographed on a 10g silica Bond-Elut column eluted with a solvent gradient (ethyl acetate-20% methanol/ethylacetate) to give the tide compound, yield 90 mg. MH+ 701.

The N-[1-(3-phenyl-3-[piperazin-1-yl]propyl)-piperidin-4-yl]-N-ethyl-4-methanesulphonylphenylacetamide (Compound 86 of Table 1) used as starting material was prepared following the method described in Example 2 using the appropriate (1-tert-butyloxycarbonyl)-piperazine analogue.

The N-[1-(3-phenyl-3-[-tert-butyloxycarbonylpiperazin-1-yl]propyl)-piperidin-4-yl]-N-ethyl-4-methanesulphonylphenylacetamide (Compound 152 of Table 1)used as starting material was prepared following the method described-in example 1 using (1-tert-butyloxycarbonyl)piperazine as the amine component

EXAMPLE 8

(R or S) N-[1-(3-phenyl-3-[(4-{2,2,2-trifluoroethylsulphonyl-piperazinyl}propyl)-piperidin-4-yl]-N-ethyl-methanesulphonylphenylacetamide (Compound Number 15 of Table 2)

Triethylamine (50 µl) was added to a solution of (R or S) N-[1-(3-phenyl-3-piperazinyl}propyl)-piperidinyl]-N-ethyl-4-methanesulphonylphenylacetamide (175 mg) in dichloromethane (5 ml ) followed by 2,2,2-trifluoroethanesulphonyl chloride (37 µl) and the mixture was stirred at room temperature for 14 hours. The reaction mixture was washed with water and dried. The residue obtained on removal of the solvent was chromatographed on a 20 g silica Bond-Elut column eluted with a solvent gradient (ethyl acetate–40% methanol/ethyl acetate) to give the title compound as a white foam, yield 79 mg, MH+ 673. NMR (CDCl$_3$): 1.2 (t, 1H), 1.3 (t, 2H), 1.4 (m, 1H), 1.6–1.8 (m,8H), 2.1 (m,2H), 2.25 (m, 1H), 2.5 (m, 4H), 2.9 (m, 2H), 3.0 (s, 3H), 3.3 (m, 5H), 3.4 (m, 1H), 3.6 (q, 2H), 3.8 (m, 2H), 7.2 (m, 2H), 7.3 (m, 3H), 7.4 (m, 2H), 7.9 (d, 2H).

EXAMPLE 9

(R or S) N-[1-(3-phenyl-3-(Boc-piperazinyl}propyl)-piperidin-4-yl]-N-ethyl-4-methanesulphonylphenylacetamide (R or S) N-[1-(3-phenyl-3-chloropropyl)-piperidin-4-yl]-N-ethyl-4-methanesulphonylphenylacetamide (594 mg) was added to a solution of triethylamine (0.35 ml) and Boc-piperazine (233 mg) in dichloromethane (10 ml) at room temperature and the mixture was stirred for 14 hours. The reaction mixture was added to a 20 g silica Bond-Elut column and was eluted with a solvent gradient (ethyl acetate–40% methanol/ethyl acetate) to give the title compound as a foam, yield 440 mg, MH+ 627.

(R or S) N-[1-(3-phenyl-3-chloropropyl)-piperidin-4-yl-4]-N-ethyl-4-methanesulphonylphenylacetamide

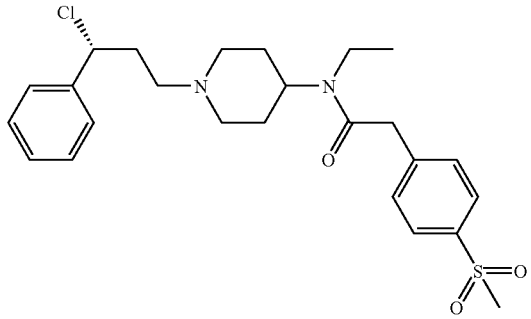

Methanesulphonyl chloride (0.5 ml) was added to a stirred mixture of S N-[1-(3-phenyl-3-hydroxypropyl)-piperidin-4-yl]-N-ethyl-4-methanesulphonylphenylacetamide (2.7 g) and triethylamine (1.64 ml) in dichloromethane (50 ml) at 0° C. and the mixture was stirred at ambient temperature for 15 hours. The reaction mixture was washed with water and dried. Removal of the solvent gave the title compound as an orange foam, yield 2.4 g, MH+ 477.

(S) N-[1-(3-phenyl-3-hydroxypropyl)-piperidin-4-yl]-N-ethyl-4-methanesulphonylphenylacetamide

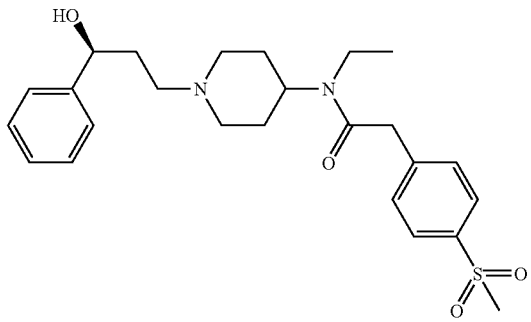

(S) 1-Phenyl-3-(4toluenesulphonyloxy)propan-1-ol (5 g) was added to a mixture of N-(piperidin-4-yl)-N-ethyl-4-methanesulphonylphenylacetamide (5.3 g) and potassium carbonate (2.71 g) in DMF (100 ml) and the mixture was stirred and heated at 80–90 °C. for 6 hours. The reaction mixture was allowed to cool and was evaporated to dryness. The residue obtained was dissolved in dichloromethane (50 ml) and was washed with water and dried. The solvent was removed and the residue was passed down a 90 g silica Bond-Elut column eluted with a solvent gradient (ethyl acetate–20% methanol/ethyl acetate) to give the title compound, yield 2.7 g, MH+ 459. NMR (CDCl$_3$): 1.2 (t, 1H), 1.3 (t,2H), 1.6 (m, 2H), 1.75 (m, 3H), 1.85 (m, 3H), 2.2 (m, 1H), 2.55–2.7 (m, 2H), 3.0 (s, 3H), 3.1–3.2 (m, 2H), 3.3(q, 2H), 3.8(m, 2H), 4.9 (m, 1H), 7.3 (m, 5H), 7.45 (d, 2H), 7.9 (d, 2H).

(S) 1-Phenyl-3-(4-toluenesulphonyloxy)propan-1-ol is a known compound (CAS No 156453-52-0)

EXAMPLE 10

(R or S) N-[1-(3-phenyl-3-piperazinyl}propyl)-piperidin-4-yl]-N-ethyl-4-methanesulphonylphenylacetamide Trifluoroacetic acid (5 ml) was added to a solution of (R or S) N-[1-(3-phenyl-3 (Boc-piperazinyl}propyl)-piperidin-4-yl]-N-ethyl-4-methanesulphonylphenylacetamide (440 mg) in dichloromethane (10 ml) and the mixture was stirred for 1 hour. The reaction mixture was concentrated and the residue was dissolved in 2M aqueous sodium hydroxide and extracted twice with dichloromethane (10 ml each time). The combined extracts were dried and evaporated to give the title compound as a foam, yield 370 mg, MH+ 527.

EXAMPLE 11

(R) N-[1-(3-phenyl-3-{1-(4chlorobenzoylpiperidin-4-yl) propyl}piperidin-4-yl]-N-ethyl-4-methanesulphonylphenylacetamide (Compound number 26 of Table 2)

To a mixture of (R) N-[1-3-phenyl-3-[piperidin-4-yl]propyl)-piperidin-4-yl]-N-ethyl-4-methanesulphonylphenylacetamide (330 mg) and MP carbonate resin (670 mg of 2.8 mg material) in dichloromethane (10 ml) was added 4-chlorobenzoyl chloride (111 mg) and the mixture was stirred at room temperature for 15 hours. The reaction mixture was filtered and MP 4-toluenesulphonic acid resin (1 g) was added to the filtrate and stirred for 30 minutes. The reaction mixture was filtered and the resin was washed successively with dichloromethane (4×10 ml), 1M MeOH/NH$_3$ (3×10 ml). The combined washings were evaporated to dryness and the residue was passed through a silica Bond-Elut column eluted with a solvent gradient (ethyl acetate-20% methanol in ethyl acetate) to give the tide compound, yield 121 mg. NMR (DMSOd6): 0.8–2.2 (m, 6H) 1.2–1.5 (m, 4H) 1.5–2.1 (m, 13H) 2.4 (m, 1H) 2.7 (m, 3H) 3.3 (m, 4H) 3.8 (d, 2H) 7–7.5 (m, 11H) 7.8 (d, 2H). Analytical HPLC on a Chiralcel OJ column (250 mm×4.6 mm) eluted with methanol showed that the chiral purity was >99%.

(R) N-[1-3-phenyl-3-[piperidin-4-yl]propyl)-piperidin-4-yl]-N-ethyl-4-methanesulphonylphenylacetamide (Compound number 35 of Table 2)

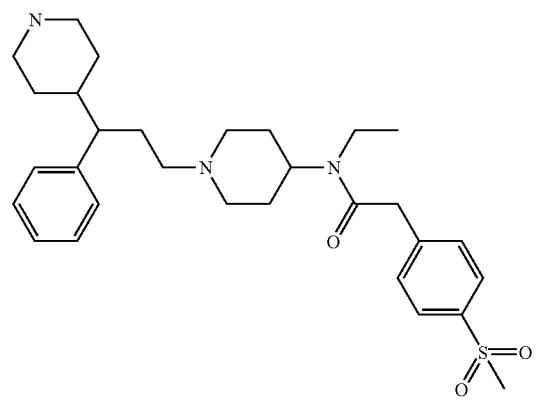

A solution of (R) N-[1–3-phenyl-3-{1-(benzyloxycarbonylpiperidin-4-yl)propyl}piperidin-4-yl]-N-ethylmethanesulphonylphenylacetamide (1.5 g) in ethanol (100 ml) containing 20% Palladium/carbon catalyst (200 mg) was hydrogenated under a hydrogen-filled balloon. The catalyst was filtered and the filtrate evaporated to dryness to give the tide compound, yield 1.1 g. MS (MH+) 526.

(R) N-[1-(3-phenyl-3-{1-(benzyloxycarbonylpiperidin-4-yl)propyl}piperidinyl]-N-ethyl-4-methanesulphonylphenylacetamide (Compound Number 24 of Table 2)

Sodium triacetoxyborohydride (890 mg) was added to a solution of (R) 3-phenyl-3-(benzyloxycarbonylpiperidin-4-yl)propionaldehyde (1.49 g) and N-(4-piperidinyl)-N-ethyl-4-methanesulphonylphenylacetamide (1.4 g) in dichloromethane (25 ml) and the mixture was stirred for 1 hour. The reaction mixture was washed with 2M NaOH (2×50 ml) and dried. The solvent was removed and the residue was passed down a silica Bond-Elut column eluted with a solvent gradient (ethyl acetate–20% methanol/ethyl acetate) to give the title compound, yield 1.5 g. MS (MH+) 660.

(R) 3-phenyl-3-(benzyloxycarbonylpiperidin-4-yl) propionaldehyde

Dess-Martin periodinane (1,1,1-triacetoxy-1,1-dihydro-1,2-benziodoxol-3(1H)-one) (1.8 g) was added to a solution of (R) 3-phenyl-3-(benzyloxycarbonylpiperidin-4-yl)propanol in dichloromethane (25 ml) and the mixture was stirred for 1 hour, washed with 2M NaOH (2×20 ml) and dried. The dichloromethane solution containing the title compound was used directly in the next stage.

(R) 3-phenyl-3-(benzyloxycarbonylpiperidin-4-yl) propanol

Lithium aluminium hydride (9.46 ml of 1M LAH in THF) was added dropwise to a solution of (R) 3-[3-phenyl-3-(benzyloxycarbonylpiperidin-4-yl)propionyl]-(4R,5S)-1,5-dimethylphenyl-2-imidazolidinone (5.1 g) in THE (100 ml) at such a rate that the temperature did not exceed 0° C. The reaction mixture was stirred at −5° C. for 10 minutes and 2M NaOH was added (10 ml). The reaction mixture was filtered through Celite and the filtrate was evaporated to dryness. The residue was dissolved in dichloromethane (20 ml) and dried. The residue obtained on removal of the solvent was passed through a Bond-Elut column eluted with a solvent gradient (isohexane—60% ethyl acetate/isohexane).to give the title compound, yield 1.6 g. MS (MH$^+$) 354.

3-[(R) 3-phenyl-3-(benzyloxycarbonylpiperidin-4-yl)propionyl]-(4R,5S)-1,5-dimethyl-4-phenyl-2-imidazolidinone

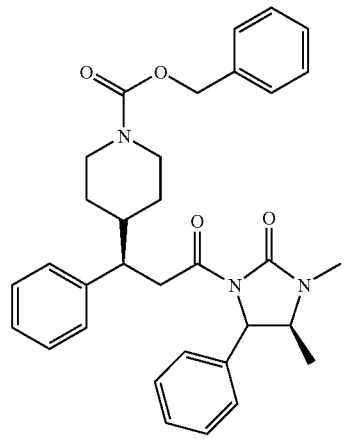

TMEDA (2.4 g) was added to a suspension of cuprous iodide (4.02 g) in TEF (100 ml) and the mixture was stirred at room temperature for 30 minutes. The reaction mixture was cooled to −78° C. and phenylmagnesium bromide (11.69 ml of a 1M solution in THF) was added and the mixture was stirred at −78° C. for 30 minutes. Dibutylboron triflate (11.69 ml, 1M solution in diethyl ether) was added to a solution of 3-[3-(benzyloxycarbonylpiperidin-4-yl)acryloyl]-4R,5S)-1,5-dimethyl-4-phenyl-2-imidazolidinone (4.9 g) in THF (50 ml) and this mixture was added dropwise over 10 minutes to the solution of the cuprate reagent. The reaction mixture was stirred at −78° C. for 1 hour then allowed to warm to ambient temperature. The solvent was evaporated, the residue was dissolved in ethyl acetate and filtered through silica (100 g). The ethyl acetate solution was washed with 2M HCl (1×100 ml), dried and evaporated to dryness. The residue was passed down a Bond-Elut column eluted with a mixture of ethyl acetate and isohexane (1:1) to give the title compound as a single diastereoisomer by NMR. Yield 5.1 g. NMR (DMSOd6): 0.5 (d, 3H) 0.8–1.1 (m.2H) 1.3 (d, 1H) 1.7 (m, 2H) 2.6 (m, 5H) 2.85–3.1 (m, 4H) 5.05 (s, 2H) 5.2 (d, 1H) 6.8 (m, 2H) 7.1–7.5 (m, 13H)

3-[3-(benzyloxycarbonylpiperidin-4-yl)acryloyl]-(4R,5S)-1,5 dimethyl-4-phenyl-2-imidazolidinone

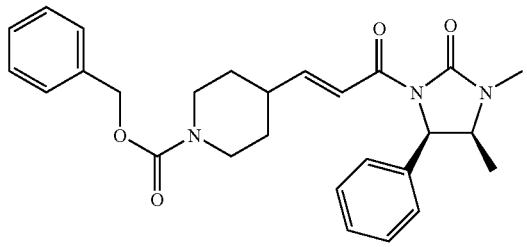

1-Chloro-N,N,2-trimethyl-1-propenylamine (1.37 g) was added dropwise over 10 minutes to a solution of 3-(benzyloxycarbonylpiperidin-4-yl)propenoic acid (2.5 g) in THF (20 ml) and the mixture was stirred for 1.5 hours. Lithium bis(trimethylsilyl)amide (8.65 ml)was added to a solution of (4R,5S)-1,5dimethyl4-phenyl-2-imidazolidinone (1.64 g) in THF (20 ml) at −10° C. and the mixture was stirred at −10° C. for 10 minutes, allowed to warm to 0° C. and then cooled again to −10° C. The acid chloride solution (prepared above) was added dropwise and the mixture was allowed to warm to room temperature. The reaction mixture was poured into water (100 ml) and extracted with ethyl acetate (3×50 ml). The combined extracts were dried, evaporated to dryness and the residue was chromatographed on a Bond-Elut column eluted with an ethyl acetate/isohexane mixture (1:1) to give the title compound, yield 3.6 g. NMR (DMSOd6): 0.6 (d, 3H) 0.95 (d, 1H) 1.2 (m, 2H) 1.55 (m, 2H) 2.4 (m, 1H) 2.3 (s, 3H) 2.8 (m, 2H) 3.95 (m, 3H) 5 (s, 2H) 5.3 (d, 1H) 6.9 (m, 1H) 7.1 (m, 2H) 7.2–7.4 (m, 8H).

3-(benzyloxycarbonylpiperidin-4-yl)propenoic acid

A mixture of N-benzyloxycarbonyl-4-formylpiperidine (10 g), malonic acid (4.2), pyridine (4 ml) and piperidine (0.4 ml) was heated at 100° C. for 2 hours. The reaction mixture was allowed to cool and was diluted with ethyl acetate (100 ml). The solution was washed with 2M HCl (2×100 ml), dried and evaporated to dryness. The residue was triturated with isohexane to give the title compound, yield 13.5 g. NMR (DMSOd6): 1.2 (m, 2H) 1.7 (m, 2H) 2.35 (m, 1H) 2.85 (m, 2H) 4 (d, 2H) 5.05 (s, 2H) 5.75 (d, 1H) 6.75 (m, 1H) 7.35 (m, 5H) 12.25 (broad peak, 1H)

EXAMPLE 12

N-[1-3-[(3-fluorophenyl)-3-[1-phenylpiperidin-4-yl]propyl)-piperidinyl-4-yl]-N-ethyl-4-methanesulphonylphenylacetamide (Compound number 145 of Table 1)

2M NaOH was added to a suspension of N-[1-[3-(3-fluorophenyl-3-[piperidin-4-yl]propyl)-piperidin-4-yl]-N-ethyl4methanesulphonylphenylacetamide di-hydrochloride salt (0.85 g) in dichloromethane (25 ml) and the mixture was stirred until a clear solution was obtained. The dichloromethane solution was dried and filtered. To this dichloromethane solution was added benzeneboronic acid (330 mg), triethylamine (280 mg) and cupric acetate (276 mg). The reaction mixture was stirred for 15 hours, washed with water and filtered through a Chem Elute cartridge. The dichloromethane filtrate was washed with 2M NaOH (3×20 ml), dried and poured on to a 20 g SCX cartridge and eluted with methanol (6×20 ml) and 1M ammonia in methanol (6×20 ml). The combined ammonia washings were evaporated and the residue obtained was chromatographed on a Bond-Elut column eluted with a solvent gradient (ethyl acetate-20% methanol/ethyl acetate to give the title compound, yield 179 mg.

The N-[1-3(3-fluorophenyl-3-[piperidin-4-yl]propyl)-piperidin-4-yl]-N-ethyl methanesulphonylphenylacetamide di-hydrochloride salt (Compound number 87 of Table 1) used as starting material was prepared following the procedures of Example 3 and Method C.

EXAMPLE 13

Racemic N-[1-(3-(3-fluorophenyl)-3-[4-(4-methanesulphonyl)phenylsulphonyl)piperazin-1-yl]propyl)-piperidin-4-yl]-N-ethyl-4-methanesulphonylphenylacetamide (78 mg) (Compound number 59 of Table 1) was separated into its single enantiomers by chromatography on a Gilson preparative HPLC using a 50 mm 20 μm Chiracel OD column eluted with a mixture of ethanol:isohexane (9:1). Less polar isomer, yield 20 mg (Compound number 16 of Table 2) More polar isomer, yield 22 mg (Compound number 17 of Table 2)

EXAMPLE 14

N1-[1-(3-phenyl)-3-{1-(ethanesulphonylpiperidin-4-yl) propyl}piperidin-4-yl]-N1-ethyl-N3-4-methanesulphonylphenylmethyl urea (Compound Number 7 of Table 3)

4-Methanesulphonylphenylmethyl isocyanate (99 mg) in TBF (10 ml) was added to 4-N-ethyl-[1-(3-phenyl)-3-{1-(ethanesulphonylpiperidin-4-yl)propyl}piperidine (200 mg) and the mixture -was allowed to stand at room temperature for 16 hours. The reaction mixture was poured on to a 5 g SCX cartridge and was eluted with dichloromethane (3×10 ml), methanol (3×10 ml) and methanolic ammonia (1M, 3×10 ml). The methanolic ammonia washings were evaporated and the residue was dissolved in dichloromethane (20 ml) and isocyanate resin (200 mg) was added. The mixture was stirred for 16 hours, filtered and the filtrate was evaporated to dryness. The residue obtained was chromatographed on a Bond-Elut column eluted with a solvent gradient (ethyl acetate-25% methanol/ethyl acetate) to give the title compound, yield 37 mg. MS (MH+) 633.

4-N-ethyl-[1-(3-phenyl)-3-{1-(ethanesulphonylpiperidin-4-yl)propyl}piperidine

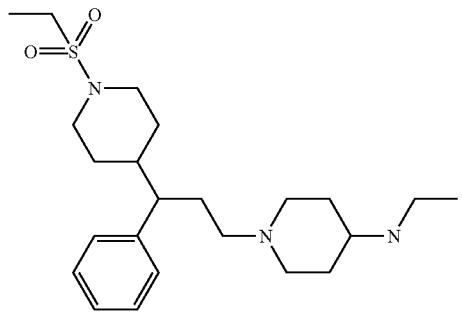

A mixture of N-ethyl-N-[1-(3-phenyl)-3-{1-(ethanesulphonylpiperidin-4-yl)propyl}piperidin-4-yl]-carbamic acid benzyl ester (5 g) and 10% Palladium on carbon (2 g) in ethanol (200 ml) was hydrogenated under a hydrogen filled balloon. The catalyst was filtered and the filtrate evaporated to dryness to give the title compound, yield 2.78 g.

N-ethyl-N-[1-(3-phenyl)-3-{1-ethanesulphonylpiperidin-4-yl)propyl}piperidin-4-yl]-carbamic acid benzyl ester

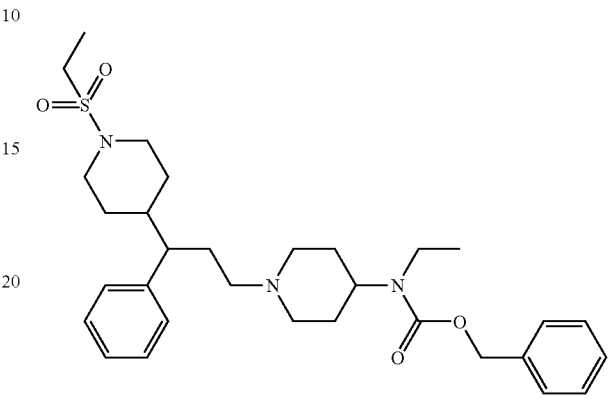

Ethanesulphonyl chloride (2.3 g) was added to a solution of N-ethyl-N-[1-(3-phenyl)-3-{piperidin-4-yl) propyl}piperidin-4-yl]-carbamic acid benzyl ester di-hydrochloride (8.5 g) and triethylamine (4.8 g) in dichloromethane (200 ml) maintained at 0° C. The reaction mixture was allowed to warm to room temperature and was stirred for 4 hours. The reaction mixture was washed with 2M NaOH (2×100 ml), dried and evaporated to dryness. The residue was chromatographed on a Bond-Elut column eluted with a solvent gradient (ethyl acetate—20% methanol/ethyl acetate) to give the title compound, yield 5 g. NMR (DM-SOd6): 1 (t, 3H) 1.1 (t, 3H) 1.3–3 (m, 14H) 2.2 (m, 1H) 2.55–2.9 (m, 5H) 2.95 (q, 2H) 3.1(q, 2H) 3.4–3.7 (m, 3H) 5.05 (s, 2H) 7.1–7.4 (m, 10H). MS (MH+) 556.

N-ethyl-N-[1-(3-phenyl)-3-{piperidin-4-yl) propyl}piperidin-4-yl]-carbamic acid benzyl ester di-hydrochloride HCl in dioxan (50 ml of 4M) was added to N-ethyl-N-[1-(3-phenyl)-3-{1-tert-butyloxycarbonylpiperidin-4-yl) propyl}piperidin-4-yl]-carbamic acid benzyl ester (26 g) at 0° C. the mixture was allowed to warm to room temperature and was stirred for 2 hours. The reaction mixture was diluted with diethyl ether (200 ml) and the precipitated solid di-hydrochloride salt was filtered and dried (hygroscopic). Yield 17 g. MS (MH+) 464.

N-ethyl-N-[1-(3-phenyl)-3-{1-tert-butyloxycarbonylpiperidin-4-yl)propyl}piperidin-4-yl]-carbamic acid benzyl ester A solution of 3-phenyl-3-(1-tert-butyloxycarbonylpiperidin-4-yl)propionaldehyde (7.8 g) [prepared following the method described in Example 11] in dichloromethane (200 ml) was added to a mixture of N-ethyl-N-piperidinylcarbamic acid benzyl ester hydrochloride (7.4 g) (CAS No 220395-87-9) and sodium acetate (2.17 g) in ethanol (50 ml) and stirred for 30 minutes. Sodium triacetoxyborohydride (5.2 g) was added in small portions over 15 minutes and stirring was continued for 2 hours. Aqueous NaOH (2M, 200 ml) was added dropwise, the dichloromethane layer was collected and washed with 2M NaOH (2×100 ml), dried and evaporated to dryness to give the title compound, yield 26 g. NMR (DMSOd6): 1 (t, 3H) 1.35 (s, 9H) 1.4–2 (m, 14H) 2.3(m, 2H) 2.6–2.7 (m, 4H) 3.15 (q, 2H) 3.4–4 (m, 3H) 5.05 (s, 2H) 7.1–7.2 (m, 10H). MS (MH$^+$) 563. 4-methanesulphonylphenylmethyl isocyanate Diphenylphosphoryl azide (260 mg) was added to a mixture of 4-methanesulphonylphenylacetic acid (200 mg) and triethylamine (191 mg) in THF (20 ml) and the reaction mixture was heated under reflux for 4 hours the reaction mixture was cooled and used directly for the next stage.

Method A

N-[1-(3-Phenyl-3-chloropropyl)-piperidin-4-yl]-N-ethylmethanesulfonylphenylacetamide Step 1: Preparation of N-[1-(3-phenyl-3-oxopropyl)-piperidin-4-yl]-N-ethyl-4-methanesulfonylphenylacetamide To a solution of N-(4-piperidinyl)-N-ethyl-4-methanesulfonylphenylacetamide (Method B; 3.24 g, 10 mmol) in DMF (50 mL) was added potassium carbonate (2.76 g, 20 mmol) followed by 3-chloropropiophenone (1.85 g, 11 mmol). The resulting mixture was stirred at room temperature for 18 h then evaporated. The residue was dissolved in DCM and the resulting solution washed with water (4×10 mL) and brine (10 mL), dried (MgSO$_4$) and evaporated to give the crude product which was purified by eluting through a 50 g Bond Elut with 10% methanol in ethyl acetate to afford the sub-titled compound (2.4 g, 53%); NMR (CDCl$_3$): 1.1 (t, 1H), 1.2 (m, 2H), 1.6 (m, 6H), 2.2 (m, 1H), 2.8 (m, 2H), 3.0 (m, 5H), 3.2 (m, 2H), 3.3 (m, 2H), 3.8 (m, 2H), 7.4 (m, 5H), 7.9 (m, 4H); MS: 457.

Step 2: Preparation of N-[1-(3-phenyl-3-hydroxypropyl)-piperidin-4-yl]-N-ethyl-4-methanesulfonylphenylacetamide To a solution of N-[1-(3-phenyl-3-oxopropylpiperidin-4-yl]-N-ethyl-4-methanesulfonylphenylacetamide (912 mg, 2 mmol) in ethanol (20 mL) at 0° C. was added sodium borohydride (76 mg, 2 mmol). The resulting mixture was stirred at room temperature for 30 min then evaporated. The residue was dissolved in DCM and the resulting solution washed with water (2×5 mL) and brine (5 mL), dried (MgSO$_4$) and evaporated to give the sub-titled compound (812 mg, 87%); NMR (CDCl$_3$): 1.1 (t, 1H), 1.2 (m, 2H), 1.6 (m, 8H), 2.0 (m, 1H), 2.2 (m, 1H) 2.6 (m, 2H), 3.0 (s,3H), 3.2 (m, 2 H), 3.3 (m, 2H), 3.8 (m, 2H), 4.9 (d, 1H), 7.3 (m, 5H), 7.4 (d, 2H), 7.9 (d, 2H); MS: 459.

Step 3: Preparation of the title compound

To a mixture of N-[1-(3-phenyl-3-hydroxypropyl)-piperidinyl]-N-ethyl-4-methanesulfonylphenylacetamide (400 mg, 0.87 mmol) and triethylamine (0.24 mL, 1.04 mmol) in DCM (10 mL) at 0° C. was added methane sulfonyl chloride (67 µL, 0.87 mmol). The resulting mixture was stirred at room temperature for 30 min. then evaporated. The residue was purified by eluting through a 20 g Bond Elut to give the title compound (180 mg, 44%); NMR (CDCl$_3$): 1.1 (t, 1H), 1.2 (m, 2H), 1.6 (m, 7H), 2.2 (m, 2H), 2.4 (m, 2H), 2.8 (m, 2H), 3.0 (s, 3H), 3.3 (m, 2H), 3.8 (m, 2H), 5.0 (m, 1H), 7.3 (m, 5H), 7.4 (d, 2H), 7.9 (d, 2H); MS: 477.

Method B
N-(4-Piperidinyl)-N-ethyl-4-methanesulfonylphenylacetamide

Step 1: Preparation of 1-phenylmethyl-4-ethylaminopiperidine dihydrochloride

To a solution of 1-phenylmethyl-4-piperidone (25.0 g, 132 mmol) in THF (250 mL) was added ethylamine hydrochloride (12.0 g, 147 mol) and methanol (50 mL) and the resulting mixture stirred at room temperature for 10 min. Sodium triacetoxyborohydride (40 g, 189 mmol) was added portionwise and the resulting mixture stirred at room temperature for 1 h. 2M Sodium hydroxide solution (250 mL) was added and the resulting mixture extracted with diethyl ether. The organic extracts were dried (K$_2$CO$_3$) and evaporated to give 1-phenylmethyl-4-ethylaminopiperidine as an oil. This was dissolved in ethanol (500 mL) and concentrated hydrochloric acid (20 mL) was added. The resulting crystals were collected, washed with diethyl ether and dried giving the sub-titled compound as a solid (38 g); NMR: (CDCl$_3$): 1.10 (t, 3H), 1.40 (m, 2H), 1.83 (m, 2H), 2.02 (m, 2H), 2.65 (q, 2H), 2.85 (m, 2H), 3.50 (s, 2H), 3.75 (m, 1H), 7.2–7.4 (m, 5H); MS: 219 (MH+).

Step 2: Preparation of N-(1-Phenylmethyl-4-piperidinyl)-N-ethyl-4-methanesulfonylphenylacetamide To a solution of 1-phenylmethyl-4-ethylaminopiperidine dihydrochloride (32.0 g, 110 mmol) in DCM (500 mL) was added N,N-diisopropylethylamine (60 mL) with stirring to ensure complete dissolution. 4-Methanesulfonylphenylacetic acid (25.0 g, 117 mmol), 4-dimethylaminopyridine (2.0 g) and dicyclohexylcarbodiimide (25.0 g, 121 mmol) were added and the resulting mixture was stirred at room temperature for 20 h. The precipitate was removed by filtration and the resulting solution was washed successively with 2N aqueous HCl, water and 1N aqueous NaOH, dried (MgSO$_4$) and evaporated. The residue was purified by silica gel chromatography (eluent 10% MeOH/ethyl acetate) to afford the sub-titled compound (35 g, 76%); NMR: 1.00 and 1.14 (t, 3H), 1.45 and 1.70 (m, 2H), 1.95 (br m, 2H), 2.80 (br m, 2H), 3.18 (s, 3H), 3.20 and 3.33 (q, 2H), 3.45 (s,2H), 3.80 and 3.87 (s, 2H), 3.70 and 4.10 (m, 1H), 7.2–7.3 (m, 5H), 7.48 (m, 2H), 7.82 (m, 2H); MS: 415 (MH+).

Step 3: Preparation of the title compound

To a solution of N-(1-phenylmethyl-4-piperidinyl)-N-ethyl-4-methanesulfonylphenyl-acetamide (34 g, 82 mmol) in ethanol (600 mL) was added ammonium formate (40 g). The mixture was purged with argon and 30% Pd on carbon (4.2 g) was added. The resulting mixture was stirred at reflux for 4 h, then allowed to cool and filtered through diatomaceous earth. The filtrate was evaporated to give a thick oil which solidified on standing to yield the title compound (24.9 g, 94%); NMR: 1.02 and 1.15 (t, 3H), 1.4–1.6 (brm, 4H), 2.45 (m, 2H), 2.93 (br m, 2H), 3.18 (s, 3H), 3.20 and 3.32 (q, 2H), 3.72 and 4.18 (m, 1H), 3.80 and 3.87 (s, 2H), 7.50 (m, 2H), 7.85 (m, 2H); MS: 325 (MH+).

Method C

3-Phenyl-3-(1-tert-butylcarbonyloxypiperidin-4-yl)propionaldehyde

Step 1: Preparation of 1-tert-butylcarbonyloxy-4-benzoylpiperidine

To a solution of 4-benzoylpiperidine (6 g, 26.5 mmol) in 2M aqueous sodium hydroxide (26.5 mL) was added di-tert-butyl dicarbonate (5.79 g, 26.5 mmol) and the resulting mixture was stirred at room temperature for 18 h. The solid product was isolated by filtration and dried under vacuum at 40° C. giving the sub-titled compound (7 g); NMR: 1.3–1.4 (m, 11H) 1.7 (m, 2H) 2.9 (m, 2H) 3.6 (m, 1H) 3.95 (m, 2H) 7.5–7.6 (m, 3H) 7.95 (d, 2H).

Step 2: Preparation of ethyl 3-phenyl-3-(1-tert-butylcarbonyloxypiperidin-4-yl)acrylate To a solution of triethylphosphonoacetate (6.2 g, 27 mmol) in THF (100 mL) at 0° C. was added lithium bis(trimethylsilyl)amide (32.5 mL, 1M, 32.5 mmol). The resulting mixture was stirred at 0° C. for 20 min. 1-tert-Butylcarbonyloxy-4-benzoylpiperidine (7 g, 25 mmol) was added and the resulting mixture was stirred at room temperature for 48 h. The mixture was evaporated and the residue dissolved in ethyl acetate (200 mL). The solution was washed with 2M hydrochloric acid (2×100 mL), dried and evaporated giving the sub-titled compound.

Step 3: Preparation of ethyl 3-phenyl-3-(1-tert-butylcarbonyloxypiperidin-4-yl)propionoate Ethyl 3-phenyl-3-(1-tert-butylcarbonyloxypiperidin-4-yl) acrylate (~25 mmol) was dissolved in ethanol (200 mL) and the solution purged with argon. 20% Palladium hydroxide (2 g) was added and the resulting mixture was stirred at room temperature under an atmosphere of hydrogen (balloon) for 72 h. The mixture was purged with argon, filtered and the filtrate evaporated. The crude product was purified by silica gel chromatography (eluent: isohexane then 35% ethyl acetate in isohexane) to give the sub-titled compound (5.3 g).

Step 4: Preparation of 3-phenyl-3-(1-tert-butylcarbonyloxypiperdin-4-yl)propan-1-ol To a solution of ethyl 3-phenyl-3-(1-tert-butylcarbonyloxypiperidin-4-yl)propionoate (5.3 g, 14.6 mmol) in THF (100 mL) was added lithium aluminium hydride (14.6 mL, 1M, 14.6 mmol) dropwise over 20 min. The resulting mixture was stirred at 0° C. for 1 h. 2M aqueous sodium hydroxide (20 mL) was added dropwise. The mixture was filtered through Celite®, washing with ethyl acetate (3×25 mL). The filtrate and washings were combined and evaporated. The residue was dissolved in ethyl acetate (100 mL) and the resulting solution washed with water (3×50 mL), dried and evaporated to give the sub-titled compound (4.6 g); NMR: 0.9–1 (m, 2H) 1.25 (m, 1H) 1.35 (s, 9H) 1.5–2 (m, 5H) 2.6 (m, 2H) 3.1 (m, 2H) 3.8-4 (m, 2H) 4.2 (t, 1H).

Step 5: Preparation of the title compound

To a solution of 3-phenyl-3-(4–1-tert-butylcarbonyloxypiperidin-4-yl)propan-1-ol (4.6 g, 14.4 mmol) in DCM (100 mL) was added Dess-Martin periodinane (6.1 g, 14.6 mmol) and the resulting mixture was stirred at room temperature for 2 h. The mixture was washed with 2M aqueous sodium hydroxide (3×50 mL), dried and evaporated to give the title compound.

Method D

N-(tert-butoxycarbonylpiperidin-4-yl]-N-ethyl methanesulphonylphenylacetamide

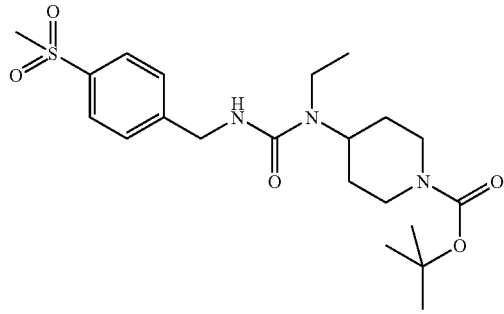

To a solution of 4-methylsulfonylphenylacetic acid (16.1 g) in toluene (200 ml) under argon was added diphenylphosphoryl azide (16.2 ml) and triethylamine (10.4 ml). The mixture was heated at 90° C. for 3 hours and then allowed to cool. The tert-butyl-1-oxo-4-aminoethyl-piperidine [CAS 264905-39-7] (17.10 g) in toluene (100 ml) was added and the mixture stirred for 18 hours and then partitioned with EtOAc/H$_2$O (500 ml/400 ml), filtered and the organic layer separated and washed with sat. NaHCO$_3$ solution. (2×300 ml), brine (300 ml), dried over MgSO$_4$, filtered and evaporated. The resulting brown oil was purified on silica using a gradient elution of 0 to 3% MeOH in EtOAc to give the title compound as a yellow solid (7.10 g); NMR: (DMSO): 1.4 (t, 3H), 1.40 (s, 9H), 1.52 (m, 4H), 2;73 (m, 2H), 3.15 (m, 5H), 4.02 (m, 3H), 4.32 (d, 2H), 6.89 (t, 1H), 7.43 (d, 2H), 7.87 (d, 2H). MS 340 (MH$^+$-Boc)

N-(piperidin-4-yl]-N-ethyl-4-methanesulphonylphenylacetamide

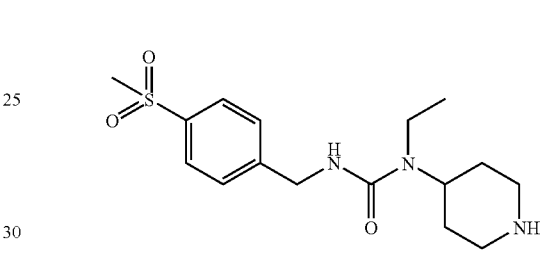

The piperidine (6.84 g) was dissolved in DCM (39 ml) and TFA (39 ml) was added slowly. The mixture was allowed to stand for 40 minutes and then evaporated. The residue was dissolved in 2M NaOH and extracted with DCM (3×150 ml) and the extracts dried over MgSO$_4$, filtered and evaporated to give the title compound as a yellow solid (5.00 g); NMR: (DMSO): 1.05 (t, 3H), 1.41 (m,4H), 2.42 (m, 2H), 2.96 (d, 2H), 3.20 (m, 5H), 3.90 (quint, 1H), 4.29 (d, 2H), 6.84 (t, 1H), 7.43 (d, 2H), 7.85 (d, 2H), MS 340 (MH$^+$).

Method E

N-[1-(3-[3,4-di-fluorophenyl]-3-hydroxypropyl)-piperidin-4-yl]-N-ethyl-4-methanesulphonylphenylacetamide

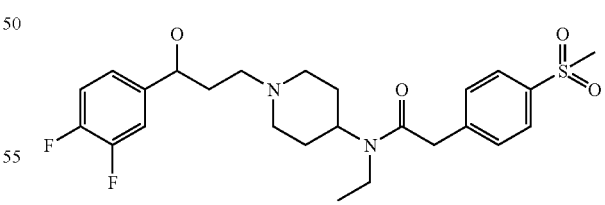

A solution of sodium borohydride (7.7 mg) in ethanol (1 ml) was added to a solution of N-[1-(3-[3,4-difluorophenyl]-3-ketopropyl)-piperidin-4-yl]-N-ethyl-4-methanesulphonylphenylacetamide (0.25 g) in ethanol (3.2 ml) at 0° C. under argon and the reaction allowed to warm to room temperature over 20 hours. The reaction was quenched with brine, extracted three times with ether and the combined extracts dried. The filtrate was then concentrated to a clear oil, yield 0.21 g. MS (MH$^+$) 495.

N-[1-(3-[3,4-difluorophenyl]-3-ketopropyl)-piperidin-4-yl]-N-ethyl-4-methanesulphonylphenylacetamide

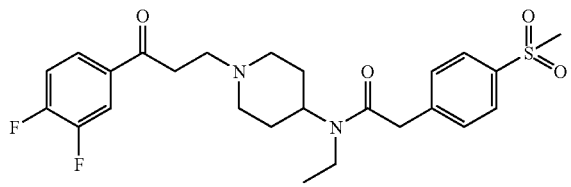

DBU was added to a solution of piperidindyl]-N-ethyl-4-methanesulphonylphenylacetamide (CAS number 374725-04-9) (320 mg) and 3,4-difluorophenylvinyl ketone (654 mg) in dicholoromethane (9 ml) under argon and the reaction mixture stirred for 36 hours. The reaction mixture was concentrated in vacuo and purified using flash column chromatography on silica eluting with a solvent gradient (methanol 10–15%, methanol in dicholormethane), yield 250 mg, MH+ 493.

3,4-difluorophenyl vinyl ketone

Dess martin periodinane (3.18 g) was added to a solution of 3,4-difluorovinyl alcohol (CAS number 149946-84-9) (1.18 g) in dicholoromethane (22 ml) at 0° C. under argon and the reaction mixture allowed to stir for 1 hour. The mixture was put directly on to a column for purification via flash column chromatography eluting with a gradient (ethyl acetate—10%, ethyl acetate and isohexane) yield 654 mg. NMR (CDCl$_3$):6.0 (d, 1H), 6.50 (d, 1H), 7.10 (dd, 1H), 7.30 (11H), 7.80 (m, 2H).

EXAMPLE 15

The ability of compounds to inhibit the binding of RANTES was assessed by an in vitro radioligand binding assay. Membranes were prepared from Chinese hamster ovary cells which expressed the recombinant human CCR5 receptor. These membranes were incubated with 0.1 nM iodinated RANTES, scintillation proximity beads and various concentrations of the compounds of the invention in 96-well plates. The amount of iodinated RANTES bound to the receptor was determined by scintillation counting. Competition curves were obtained for compounds and the concentration of compound which displaced 50% of bound iodinated RANTES was calculated (IC$_{50}$). Preferred compounds of formula (I) have an IC$_{50}$ of less than 50 µM.

EXAMPLE 16

The ability of compounds to inhibit the binding of MIP-1α was assessed by an in vitro radioligand binding assay. Membranes were prepared from Chinese hamster ovary cells which expressed the recombinant human CCR5 receptor. These membranes were incubated with 0.1 nM iodinated MIP-1α, scintillation proximity beads and various concentrations of the compounds of the invention in 96-well plates. The amount of iodinated MMP-1α bound to the receptor was determined by scintillation counting. Competition curves were obtained for compounds and the concentration of compound which displaced 50% of bound iodinated MIP-1α was calculated (IC$_{50}$). Preferred compounds of formula (I) have an IC$_{50}$ of less than 50 µM.

Results from this test for certain compounds of the invention are presented in Table VII. In Table VII the results are presented as Pic50 values. A Pic50 value is the negative log (to base 10) of the IC$_{50}$ results, so an IC50 of 1 µM (that is 1×10$^{-6}$ M) gives a Pic50 of 6. If a compound was tested more than once then the data below is an average of the probative tests results.

TABLE VII

| Compound No. | Table No | Pic50 |
|---|---|---|
| 4 | I | 7.84 |
| 6 | I | 6.44 |
| 7 | I | 8.0 |
| 9 | I | 6.51 |
| 12 | I | 6.47 |
| 18 | I | 8.05 |
| 24 | I | 8.78 |
| 27 | I | 8.9 |
| 34 | I | 7.23 |
| 37 | I | 7.84 |
| 42 | I | 9.2 |
| 45 | I | 8.3 |
| 65 | I | 8.37 |
| 69 | I | 8.85 |
| 99 | I | 8.2 |
| 142 | I | 8.63 |
| 15 | II | 8.25 |
| 18 | II | 8.46 |
| 3 | III | 8.25 |
| 47 | III | 8.23 |

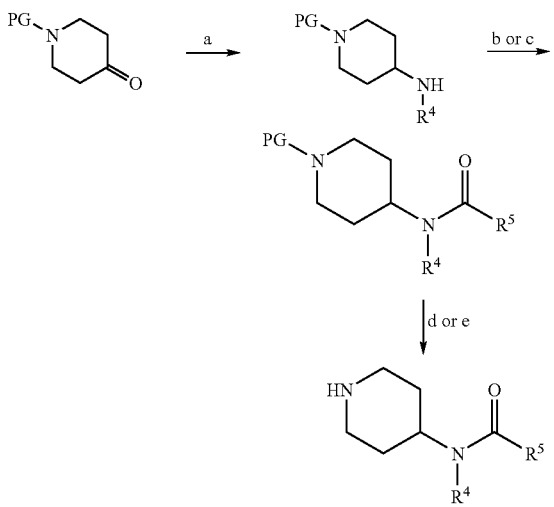

SCHEME 1

Conditions
a) Reductive amination (R$^4$NH$_2$, NaBH(OAc)$_3$)
b) Amide formation (R$^5$CO$_2$H, coupling agent or R$^5$COCl, base)
c) Urea formation (isocyanate)
d) H$_2$, Pd (PG is Bn or Bz)
e) HCl or TFA (PG is Boc)

SCHEME 2
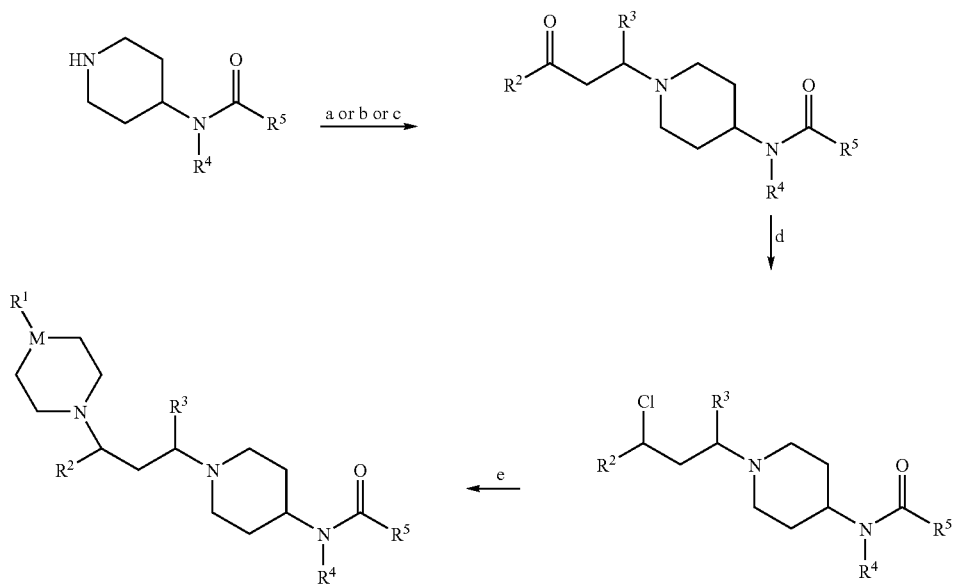
Conditions
a) Alkyl halide, base
b) R²C(=O)CH₂, R³CHO, AcOH
c) R²C(=O)CH=CHR³
d) Reduction then MsCl, base
e) Cyclic amine, base, NaI
SCHEME 3
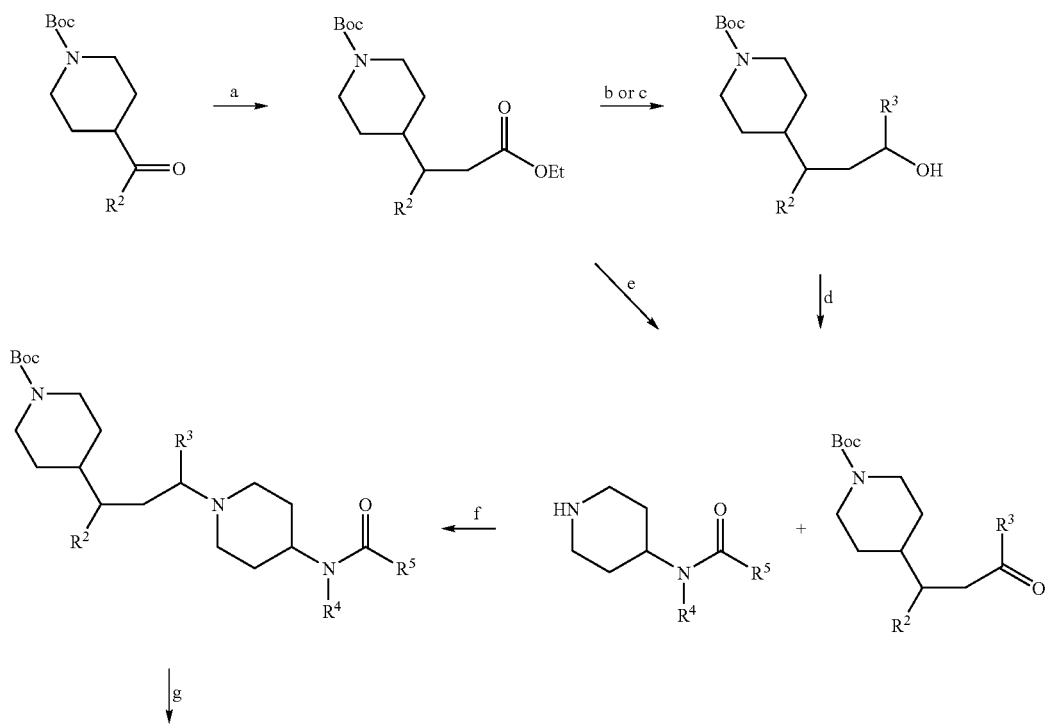

-continued

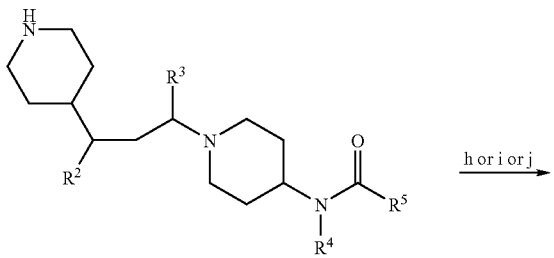

Conditions
a) (i) (EtO)₂P(=O)CH₂CO₂Et, base; (ii) hydrogenation (e.g. Pd(OH)₂, H₂)
b) Reduction (e.g. LiAlH₄) (R³ is H)
c) (i) Reduction to aldehyde (e.g. DIBAL—H); (ii) R³MgBr
d) Oxidation (e.g. Dess-Martin periodinane)
e) (i) MeONHMe, AlMe₃; (ii) Reduction (R³ is H) or R³MgBr
f) Reductive amination (NaBH(OAc)₃, AcOH)
g) HCl or TFA
h) Amide formation (acid & coupling reagent or acid halide, base)
i) Sulfonamide formation (sulfonyl chloride, base)
j) Reductive amination (aldehyde, NaBH(OAc)₃)

The invention claimed is:

1. A compound of formula (I):

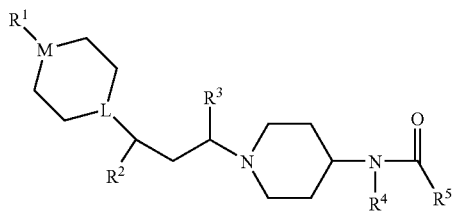

wherein

L is CH or N; M is CH or N; provided that L and M are not both CH; and provided that L and M are not both N;

$R^1$ is hydrogen, $C_{1-6}$ alkyl [optionally substituted by phenyl {which itself optionally substituted by halo, $C_{1-4}$ alkyl, $C_{1-4}$ alkoxy, cyano, nitro, $CF_3$, $OCF_3$, ($C_{1-4}$ alkyl)C(O)NH, S(O)₂NH₂, $C_{1-4}$ alkylthio, S(O)($C_{1-4}$ alkyl) or S(O)₂($C_{1-4}$ alkyl)} or heteroaryl {which itself optionally substituted by halo, $C_{1-4}$ alkyl, $C_{1-4}$ alkoxy, cyano, nitro, $CF_3$, ($C_{1-4}$ alkyl)C(O)NH, S(O)₂NH₂, $C_{1-4}$ alkylthio, S(O)($C_{1-4}$ alkyl) or S(O)₂($C_{1-4}$ alkyl)}], phenyl {optionally substituted by halo, $C_{1-4}$ alkyl, $C_{1-4}$ alkoxy, cyano, nitro, $CF_3$, $OCF_3$, ($C_{1-4}$ alkyl)C(O)NH, S(O)₂NH₂, $C_{1-4}$ alkylthio, S(O)($C_{1-4}$ alkyl) or S(O)₂($C_{1-4}$ alkyl)}, heteroaryl {optionally substituted by halo, $C_{1-4}$ alkyl, $C_{1-4}$ alkoxy, cyano, nitro, $CF_3$, ($C_{1-4}$ alkyl)C(O)NH, S(O)₂NH₂, $C_{1-4}$ alkylthio, S(O)($C_{1-4}$ alkyl) or S(O)₂($C_{1-4}$ alkyl)}, S(O)₂R⁶, S(O)₂NR¹⁰R¹¹, C(O)R⁷, C(O)₂($C_{1-6}$ alkyl), C(O)₂(phenyl($C_{1-2}$ alkyl)) or C(O)NHR⁷; and when M is CH R¹ can also be NHS(O)₂R⁶, NHS(O)₂NHR⁷, NHC(O)R⁷ or NHC(O)NHR⁷;

$R^2$ is phenyl or heteroaryl, either of which is optionally substituted by halo, $C_{1-4}$ alkyl, $C_{1-4}$ alkoxy, S(O)$_n$($C_{1-4}$ alkyl), nitro, cyano or $CF_3$;

$R^3$ is hydrogen or $C_{1-4}$ alkyl;

$R^4$ is hydrogen, methyl, ethyl, allyl or cyclopropyl;

$R^5$ is phenyl, heteroaryl, phenylNH, heteroarylNH, phenyl($C_{1-2}$)alkyl, heteroaryl($C_{1-2}$)alkyl, phenyl($C_{1-2}$ alkyl)NH or heteroaryl($C_{1-2}$ alkyl)NH; wherein the phenyl and heteroaryl rings of R⁵ are optionally substituted by halo, cyano, nitro, hydroxy, $C_{1-4}$ alkyl, $C_{1-4}$ alkoxy, S(O)$_k$($C_{1-4}$ alkyl), S(O)₂NR⁸R⁹, NHS(O)₂($C_{1-4}$ alkyl), NH₂, NH($C_{1-4}$ alkyl), N($C_{1-4}$ alkyl)₂, NHC(O)NH₂, C(O)NH₂, C(O)NH($C_{1-4}$ alkyl), NHC(O)($C_{1-4}$ alkyl), CO₂H, CO₂($C_{1-4}$ alkyl), C(O)($C_{1-4}$ alkyl), $CF_3$, $CHF_2$, $CH_2F$, $CH_2CF_3$ or $OCF_3$;

k, m and n are, independently, 0, 1 or 2;

$R^6$ is $C_{1-6}$ alkyl [optionally substituted by halo, $C_{1-4}$ alkoxy, phenyl {which itself optionally substituted by halo, $C_{1-4}$ alkyl, $C_{1-4}$ alkoxy, cyano, nitro, $CF_3$, $OCF_3$, ($C_{1-4}$ alkyl)C(O)NH, S(O)₂NH₂, $C_{1-4}$ alkylthio, S(O)($C_{1-4}$ alkyl) or S(O)₂($C_{1-4}$ alkyl)} or heteroaryl {which itself optionally substituted by halo, $C_{1-4}$ alkyl, $C_{1-4}$ alkoxy, cyano, nitro, $CF_3$, ($C_{1-4}$ alkyl)C(O)NH, S(O)₂NH₂, $C_{1-4}$ alkylthio, S(O)($C_{1-4}$ alkyl) or S(O)₂($C_{1-4}$ alkyl)}], $C_{3-7}$ cycloalkyl, pyranyl, phenyl {optionally substituted by halo, $C_{1-4}$ alkyl, $C_{1-4}$ alkoxy, cyano, nitro, $CF_3$, $OCF_3$, ($C_{1-4}$ alkyl)C(O)NH, S(O)₂NH₂, $C_{1-4}$ alkylthio, S(O)($C_{1-4}$ alkyl) or S(O)₂($C_{1-4}$ alkyl)} or heteroaryl {optionally substituted by halo, $C_{1-4}$ alkyl, $C_{1-4}$ alkoxy, cyano, nitro, $CF_3$, ($C_{1-4}$ alkyl)C(O)NH, S(O)₂NH₂, $C_{1-4}$ alkylthio, S(O)($C_{1-4}$ alkyl) or S(O)₂($C_{1-4}$ alkyl)};

$R^7$ is hydrogen, $C_{1-6}$ alkyl [optionally substituted by halo, $C_{1-4}$ alkoxy, phenyl {which itself optionally substituted by halo, $C_{1-4}$ alkyl, $C_{1-4}$ alkoxy, cyano, nitro, $CF_3$, $OCF_3$, ($C_{1-4}$ alkyl)C(O)NH, S(O)₂NH₂, $C_{1-4}$ alkylthio, S(O)($C_{1-4}$ alkyl) or S(O)₂($C_{1-4}$ alkyl)} or heteroaryl {which itself optionally substituted by halo, $C_{1-4}$ alkyl, $C_{1-4}$ alkoxy, cyano, nitro, $CF_3$, ($C_{1-4}$ alkyl)C(O)NH, S(O)₂NH₂, $C_{1-4}$ alkylthio, S(O)($C_{1-4}$ alkyl) or S(O)₂($C_{1-4}$ alkyl)}], $C_{3-7}$ cycloalkyl, pyranyl, phenyl {optionally substituted by halo, $C_{1-4}$ alkyl, $C_{1-4}$ alkoxy, cyano, nitro, $CF_3$, $OCF_3$, ($C_{1-4}$ alkyl)C(O)NH, S(O)₂NH₂, $C_{1-4}$ alkylthio, S(O)($C_{1-4}$ alkyl) or S(O)₂($C_{1-4}$ alkyl)} or heteroaryl {optionally substituted by halo, $C_{1-4}$ alkyl, $C_{1-4}$ alkoxy, cyano, nitro, $CF_3$, ($C_{1-4}$ alkyl)C(O)NH, S(O)₂NH₂, $C_{1-4}$ alkylthio, S(O)($C_{1-4}$ alkyl) or S(O)₂($C_{1-4}$ alkyl)};

R[8] and R[9] are, independently, hydrogen or $C_{1-4}$ alkyl, or together with a nitrogen or oxygen atom, may join to form a 5- or 6-membered ring which is optionally substituted with $C_{1-4}$ alkyl, C(O)H or C(O)($C_{1-4}$ alkyl);

R[10] and R[11] are, independently, hydrogen or $C_{1-4}$ alkyl, or may join to form a 5- or 6-membered ring which is optionally substituted with $C_{1-4}$ alkyl or phenyl (wherein the phenyl ring is optionally substituted by halo, cyano, nitro, hydroxy, $C_{1-4}$ alkyl, $C_{1-4}$ alkoxy, $S(O)_m C_{1-4}$ alkyl, $S(O)_2 NH_2$, $S(O)_2 NH(C_{1-4}$ alkyl), $S(O)_2 N(C_{1-4}$ alkyl)$_2$, $NHS(O)_2(C_{1-4}$ alkyl), $NH_2$, $NH(C_{1-4}$ alkyl), $N(C_{1-4}$ alkyl)$_2$, $NHC(O)NH_2$, $C(O)NH_2$, $C(O)NH(C_{1-4}$ alkyl), $NHC(O)(C_{1-4}$ alkyl), $CO_2H$, $CO_2(C_{1-4}$ alkyl), $C(O)(C_{1-4}$ alkyl), $CF_3$, $CHF_2$, $CH_2F$, $CH_2CF_3$ or $OCF_3$);

or a pharmaceutically acceptable salt thereof;

provided that when R[1] is hydrogen or unsubstituted alkyl, R[4] is hydrogen, methyl or ethyl, L is CH and M is N, then the phenyl or heteroaryl part of R[5] is substituted by one of: $S(O)_k C_{1-4}$ alkyl, $NHC(O)NH_2$, $C(O)(C_{1-4}$ alkyl), $CHF_2$, $CH_2F$, $CH_2CF_3$ or $OCF_3$, and optionally further substituted by one or more of halo, cyano, nitro, hydroxy, $C_{1-4}$ alkyl, $C_{1-4}$ alkoxy, $S(O)_k C_{1-4}$ alkyl, $S(O)_2 NR^8 R^9$, $NHS(O)_2(C_{1-4}$ alkyl), $NH_2$, $NH(C_{1-4}$ alkyl), $N(C_{1-4}$ alkyl)$_2$, $NHC(O)NH_2$, $C(O)NH_2$, $C(O)NH(C_{1-4}$ alkyl), $NHC(O)(C_{1-4}$ alkyl), $CO_2H$, $CO_2(C_{1-4}$ alkyl), $C(O)(C_{1-4}$ alkyl), $CF_3$, $CHF_2$, $CH_2F$, $CH_2CF_3$ or $OCF_3$.

2. A compound as claimed in claim 1 wherein L is CH.

3. A compound as claimed in claim 1 wherein M is N.

4. A compound as claimed in claim 1 wherein R[1] is phenyl (optionally substituted by halo, $C_{1-4}$ alkyl, $C_{1-4}$ alkoxy, $CF_3$ or $OCF_3$), $S(O)_2(C_{1-4}$ alkyl), $S(O)_2(C_{1-4}$ fluoroalkyl), $S(O)_2$ phenyl (optionally substituted by halo, cyano, $C_{1-4}$ alkyl, $C_{1-4}$ alkoxy, $CF_3$, $OCF_3$, $S(O)_2(C_{1-4}$ alkyl) or $S(O)_2(C_{1-4}$ fluoroalkyl)), benzyl (optionally substituted by halo, $C_{1-4}$ alkyl, $C_{1-4}$ alkoxy, $CF_3$ or $OCF_3$), benzoyl (optionally substituted by halo, $C_{1-4}$ alkyl, $C_{1-4}$ alkoxy, $CF_3$ or $OCF_3$), C(O)NHphenyl (optionally substituted by halo, $C_{1-4}$ alkyl, $C_{1-4}$ alkoxy, $CF_3$ or $OCF_3$), $S(O)_2$thiophenyl, $CH_2$pyridinyl, $CH_2$quinolinyl or $CH_2$thiazolyl.

5. A compound as claimed in claim 1 wherein R[2] is phenyl optionally substituted by halo.

6. A compound as claimed in claim 1 wherein R[3] is hydrogen or methyl.

7. A compound as claimed in claim 1 wherein R[4] is ethyl.

8. A compound as claimed in claim 1 wherein R[5] is phenyl($C_{1-2}$)alkyl, phenyl($C_{1-2}$ alkyl)NH, phenyl, heteroaryl or heteroaryl($C_{1-2}$)alkyl; wherein the phenyl and heteroaryl rings are optionally substituted by halo, cyano, nitro, hydroxy, $C_{1-4}$ alkyl, $C_{1-4}$ alkoxy, $S(O)_k C_{1-4}$ alkyl, $S(O)_2 NR^8 R^9$, $NHS(O)_2(C_{1-4}$ alkyl), $NH_2$, $NH(C_{1-4}$ alkyl), $N(C_{1-4}$ alkyl)$_2$, $NHC(O)NH_2$, $C(O)NH_2$, $C(O)NH(C_{1-4}$ alkyl), $NHC(O)(C_{1-4}$ alkyl), $CO_2H$, $CO_2(C_{1-4}$ alkyl), $C(O)(C_{1-4}$ alkyl), $CF_3$, $CHF_2$, $CH_2F$, $CH_2CF_3$ or $OCF_3$; and R[8] and R[9] are, independently, hydrogen or $C_{1-4}$ alkyl, or together with a nitrogen or oxygen atom, may join to form a 5- or 6-membered ring which is optionally substituted with $C_{1-4}$ alkyl, C(O)H or C(O)($C_{1-4}$ alkyl); and k is 0, 1 or 2.

9. A process for preparing of a compound as claimed in claim 1 comprising:

i. where L is N, reacting a compound of formula (II):

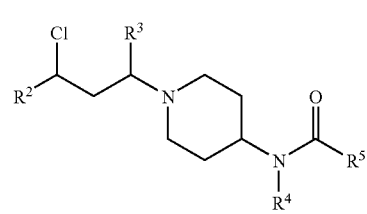

(II)

with a compound of formula (III):

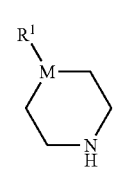

(III)

in the presence of sodium iodide and a suitable base, in a suitable solvent;

ii. where L is CH, reacting a compound of formula (IV):

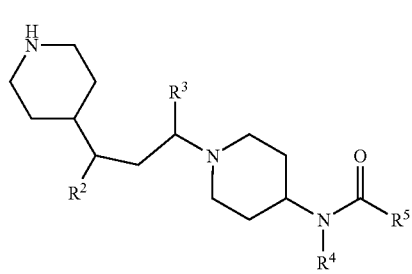

(IV)

with:

a) an acid of formula $R^1 CO_2 H$ in the presence of a suitable coupling agent in the presence of a suitable base in a suitable solvent;

b) an acid chloride of formula $R^1 C(O)Cl$ or sulphonyl chloride of formula $R^1 S(O)_2 Cl$, in the presence of a suitable base in a suitable solvent; or, c) an aldehyde of formula $R^1 CHO$ in the presence of $NaBH(OAc)_3$ (wherein Ac is $C(O)CH_3$) and acetic acid, in a suitable solvent;

iii. coupling a compound of formula (V):

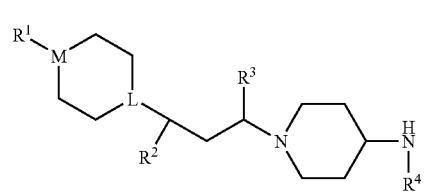

(V)

with:

a) an acid of formula $R^5CO_2H$ in the presence of a suitable coupling agent in the presence of a suitable base in a suitable solvent; or, b) an acid chloride of formula $R^5C(O)Cl$, in the presence of a suitable base in a suitable solvent.

10. A pharmaceutical composition which comprises a compound as claimed in claim 1, or a pharmaceutically acceptable salt thereof, and a pharmaceutically acceptable adjuvant, diluent or carrier.

11. An intermediate of formula (V):

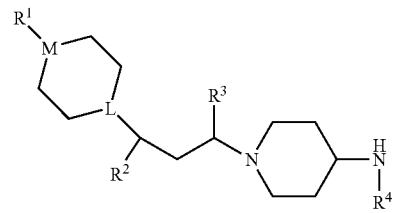

(V)

wherein L, M, $R^1$, $R^2$, $R^3$ and $R^4$ are as defined in claim 1.

* * * * *